(12) United States Patent
Schramm et al.

(10) Patent No.: US 10,118,928 B2
(45) Date of Patent: Nov. 6, 2018

(54) TREATMENT OF H. PYLORI INFECTIONS USING MTAN INHIBITORS

(71) Applicants: ALBERT EINSTEIN COLLEGE OF MEDICINE, INC., Bronx, NY (US); VICTORIA LINK LIMITED, Wellington (NZ)

(72) Inventors: Vern L. Schramm, New Rochelle, NY (US); Keith Clinch, Lower Hutt (NZ); Shivali Ashwin Gulab, Wellington (NZ)

(73) Assignees: Albert Einstein College of Medicine, Inc., Bronx, NY (US); Victoria Link Limited, Wellington (NZ)

(*) Notice: Subject to any disclaimer, the term of this patent is extended or adjusted under 35 U.S.C. 154(b) by 0 days.

(21) Appl. No.: 15/118,113

(22) PCT Filed: Feb. 6, 2015

(86) PCT No.: PCT/US2015/014778
§ 371 (c)(1),
(2) Date: Aug. 11, 2016

(87) PCT Pub. No.: WO2015/123101
PCT Pub. Date: Aug. 20, 2015

(65) Prior Publication Data
US 2017/0166571 A1 Jun. 15, 2017

Related U.S. Application Data

(60) Provisional application No. 61/938,755, filed on Feb. 12, 2014.

(51) Int. Cl.
C07D 487/04 (2006.01)
A61K 31/519 (2006.01)
C07D 471/04 (2006.01)
A61P 31/04 (2006.01)

(52) U.S. Cl.
CPC .......... *C07D 487/04* (2013.01); *A61K 31/519* (2013.01); *C07D 471/04* (2013.01); *Y02A 50/471* (2018.01); *Y02A 50/473* (2018.01); *Y02A 50/475* (2018.01); *Y02A 50/481* (2018.01)

(58) Field of Classification Search
CPC ............................ C07D 487/04; A61K 31/519
See application file for complete search history.

(56) References Cited

U.S. PATENT DOCUMENTS

| | | | |
|---|---|---|---|
| 5,985,848 A | 11/1999 | Furneaux et al. | |
| 6,066,722 A | 5/2000 | Furneaux et al. | |
| 6,228,847 B1 | 5/2001 | Furneaux et al. | |
| 6,492,347 B2 | 12/2002 | Furneaux et al. | |
| 6,803,455 B2 | 10/2004 | Furneaux et al. | |
| 7,098,334 B2 | 8/2006 | Furneaux et al. | |
| 7,211,653 B2 | 5/2007 | Furneaux et al. | |
| 7,390,890 B2 | 6/2008 | Furneaux et al. | |
| 7,553,839 B2 | 6/2009 | Furneaux et al. | |
| 8,173,662 B2 | 5/2012 | Furneaux et al. | |
| 8,183,019 B2 | 5/2012 | Lenz et al. | |
| 8,283,345 B2 | 10/2012 | Furneaux et al. | |
| 8,383,636 B2 | 2/2013 | Evans et al. | |
| 8,541,567 B2 | 9/2013 | Schramm | |
| 8,853,224 B2 | 10/2014 | Clinch et al. | |
| 9,290,501 B2 | 3/2016 | Schramm et al. | |
| 9,493,465 B2 | 11/2016 | Evans et al. | |
| 9,522,159 B2 | 12/2016 | Schramm et al. | |
| 2011/0046167 A1* | 2/2011 | Clinch .................. | C07D 487/04 514/265.1 |
| 2011/0190265 A1 | 8/2011 | Schramm | |
| 2012/0157479 A1 | 6/2012 | Evans et al. | |
| 2013/0274220 A1 | 10/2013 | Schramm et al. | |
| 2015/0210701 A1 | 7/2015 | Schramm et al. | |
| 2015/0274741 A1 | 10/2015 | Evans et al. | |

FOREIGN PATENT DOCUMENTS

| | | |
|---|---|---|
| WO | 2008030118 A1 | 3/2008 |
| WO | 2008115531 A1 | 9/2008 |
| WO | 2010033236 A2 | 3/2010 |

OTHER PUBLICATIONS

PCT International Search Report and Written Opinion, dated May 1, 2015 in connection with PCT International Application No. PCT/US2016/014778, 10 pages.
Third Party Observation dated Oct. 12, 2015 in connection with PCT International Application No. PCT/US2015/014778, 3 pages.
Gutierrez J A et al., entitled "Transition state analogs of 5'-methylthioadenosine nucleosidase disrupt quorum sensing," Nature Chemical Biology, vol. 5, No. 4, Apr. 2009, 251-257.
Li X et al., entitled "5'-Methylthioadenosine Nucleosidase Is Implicated in Playing a Key Role in a Modified Futalosine Pathway for Menaquinone Biosynthesis in Campylobacter Jejuni," the Journal of Biological Chemistry, vol. 286, No. 22, Jun. 3, 2011, 19392-19398.
Wang S et al., entitled "A picomolar transition state analogue inhibitor of MTAN as a specific antibiotic for H. pylori," Biochemistry, Sep. 4, 2012; 51(35): 6892-6894.

(Continued)

*Primary Examiner* — Susanna Moore
(74) *Attorney, Agent, or Firm* — Amster, Rothstein & Ebenstein LLP

(57) ABSTRACT

Methods of treating infections due to *Helicobacter pylori* (*H. pylori*), in particular in subjects having a peptic ulcer, are disclosed where the methods comprise administering inhibitors of *H. pylori* MTAN (5'-methylthioadenosine nucleosidase) to the subject, where the inhibitors have the structure

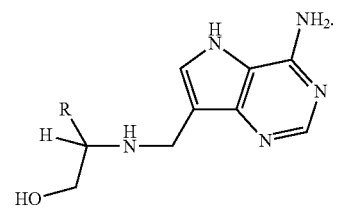

22 Claims, 1 Drawing Sheet

(56) References Cited

OTHER PUBLICATIONS

Communication Supplemental European Search Report dated Nov. 10, 2017 in connection with European Patent Application No. 15748925.3, 7 pages.

Clinch K et al., entitled "Transition state analogue inhibitors of human methylthioadenosine phosphorylase and bacterial methylthioadenosine/S-adenosylhomocysteine nucleosidase incorporating acyclic ribooxacarbenium ion mimics," Bioorganic & Medicinal Chemistry 20 (2012) 5181-5187.

* cited by examiner

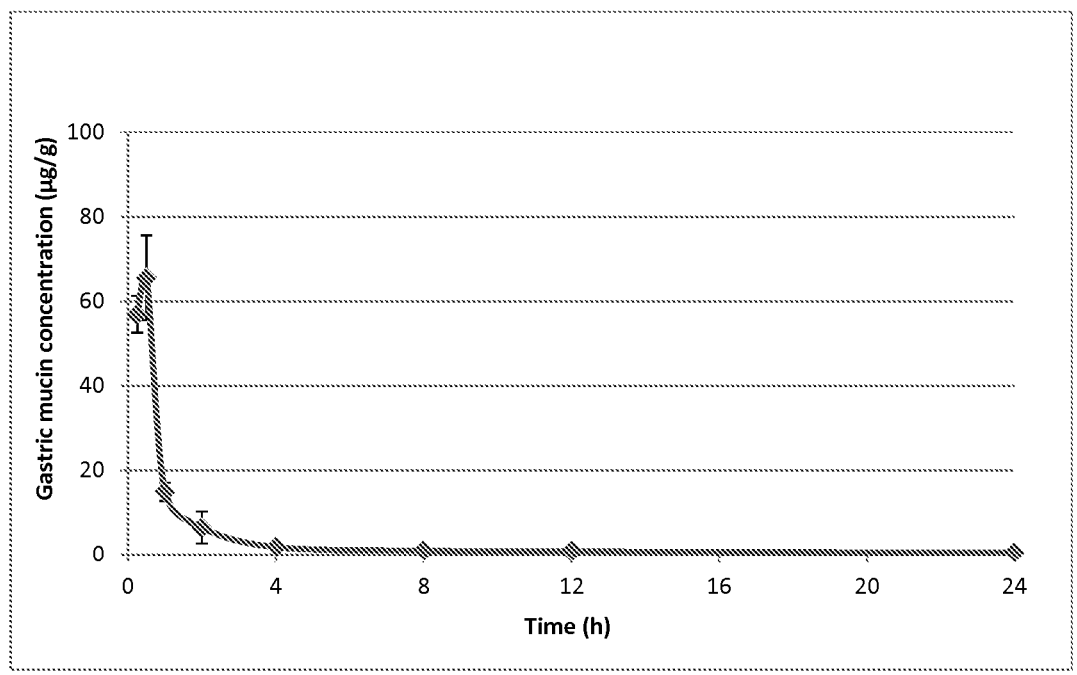

TREATMENT OF H. PYLORI INFECTIONS USING MTAN INHIBITORS

CROSS-REFERENCE TO RELATED APPLICATIONS

This application is a U.S. national stage entry under 35 U.S.C. § 371 of PCT International Patent Application No. PCT/US2015/014778, filed Feb. 6, 2015, which claims the benefit of U.S. Provisional Patent Application No. 61/938,755, filed Feb. 12, 2014, the contents of which are incorporated herein by reference into the subject application.

STATEMENT OF GOVERNMENT SUPPORT

This invention was made with government support under grant numbers GM041916 and EB009998 awarded by the National Institutes of Health. The government has certain rights in the invention.

FIELD OF THE INVENTION

The invention relates to treating infections due to *Helicobacter pylori* (*H. pylori*) using inhibitors of *H. pylori* MTAN (5'-methylthioadenosine nucleosidase), in particular in subjects having a peptic ulcer.

BACKGROUND OF THE INVENTION

Throughout this application various publications are referred to in superscripts. Full citations for these references may be found at the end of the specification before the claims. The disclosures of these publications are hereby incorporated by reference in their entireties into the subject application to more fully describe the art to which the subject application pertains.

*H. pylori* is a gram-negative bacterium and lives microaerophilically in the gastric mucosa of its human host. It is related to 85 percent of gastric and 95 percent of duodenal ulcers[1]. Drug resistance is prevalent in clinical isolates of *H. pylori*. After less than thirty years of specific antibiotic treatment, it is increasingly difficult to eradicate *H. pylori* using a combination of two antibiotics with two weeks therapy[2]. Antibiotics with new targets and mechanisms of action are needed to treat *H. pylori* infections.

Gram negative bacteria are dependent on menaquinone as electron transporters in respiration and have maintained biosynthetic pathways for these essential metabolites[3]. In contrast, humans lack the pathway of menaquinone synthesis, and targeting the menaquinone pathway provides an anti-bacterial drug design approach. Recently, a menaquinone synthetic pathway has been proposed in *Campylobacter* and *Helicobacter* that differs from most bacteria[4,5]. In this pathway, 6-amino-6-deoxyfutalosine is synthesized by MqnA and cleaved at the N-ribosidic bond by a MTAN with specificity also extending to 5'-methylthioadenosine and adenosylhomocysteine as well as 6-amino-6-deoxyfutalosine. HpMTAN converts 6-amino-6-deoxyfutalosine to adenine and dehypoxanthine futalosine, the latter being used as the processor of menaquinone synthesis. The early reactions of this pathway do not exist in the normal bacterial flora of humans, making enzymes catalyzing these reactions appealing drug targets. HpMTAN is closely related to the 5'-methylthioadenosine/S-adenosylhomocysteine hydrolases (MTANs) found in other bacteria. The well-characterized MTANs are associated with quorum sensing and S-adenosylmethionine recycling in most species and are not essential for bacterial growth[6]. Transition state analogue inhibitors of picomolar to femtomolar affinity have been developed to interrupt bacterial functions associated with quorum sensing[6,7].

The present invention addresses the need for new compounds that selectively block the growth of *H. pylori*.

SUMMARY OF THE INVENTION

The invention provides methods of treating a *Helicobacter pylori* (*H. pylori*) infection in a subject comprising administering to the subject a compound of formula (I) in an amount effective to inhibit growth of *H. pylori*, wherein formula (I) is

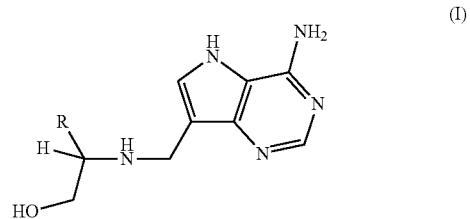

wherein R is Q or CH$_2$SQ, wherein Q is C1-C9 alkyl aryl, heteroaryl, aralkyl, or C4-C7 cycloalkyl and wherein Q is optionally substituted with one or more halogen, OH and/or NH$_2$ groups, or a pharmaceutically acceptable salt thereof, or an ester thereof.

The invention further provides a compound having the structure:

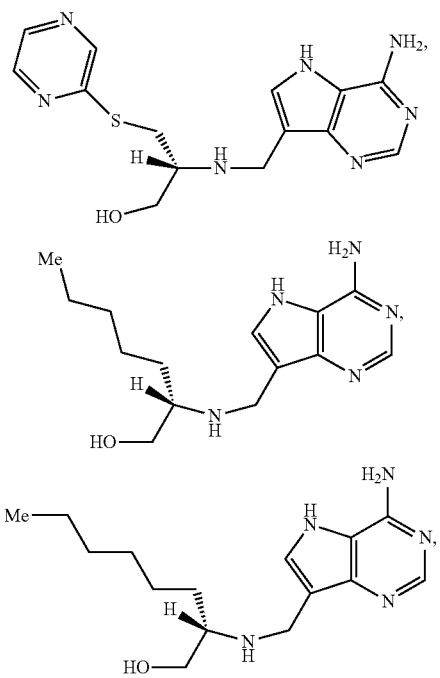

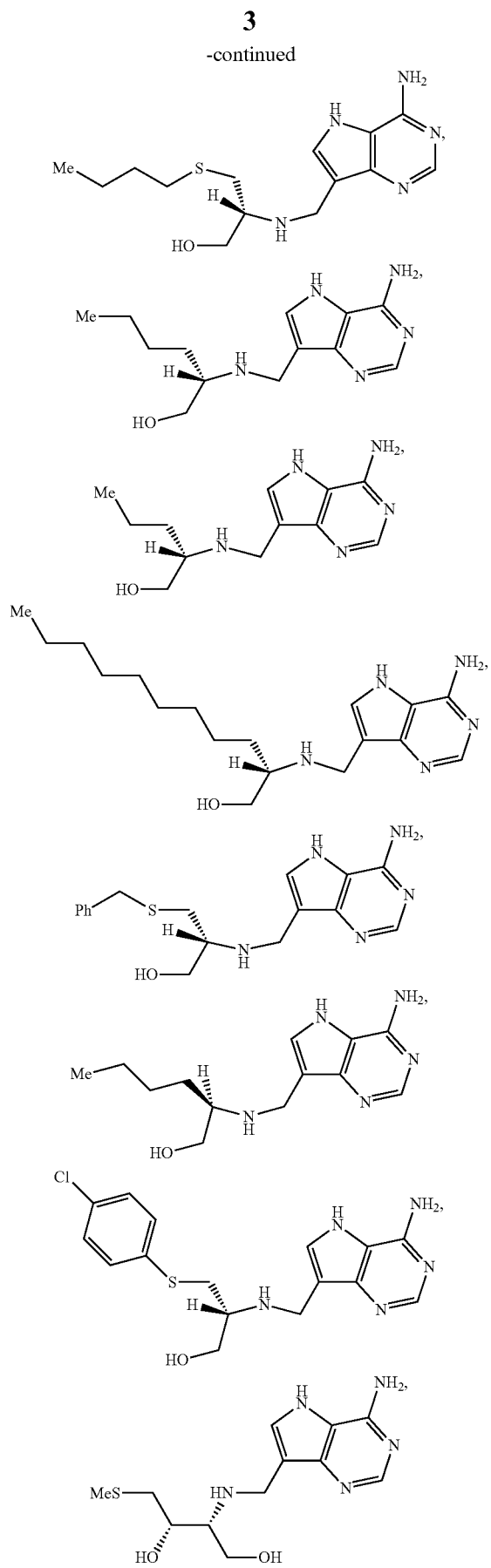
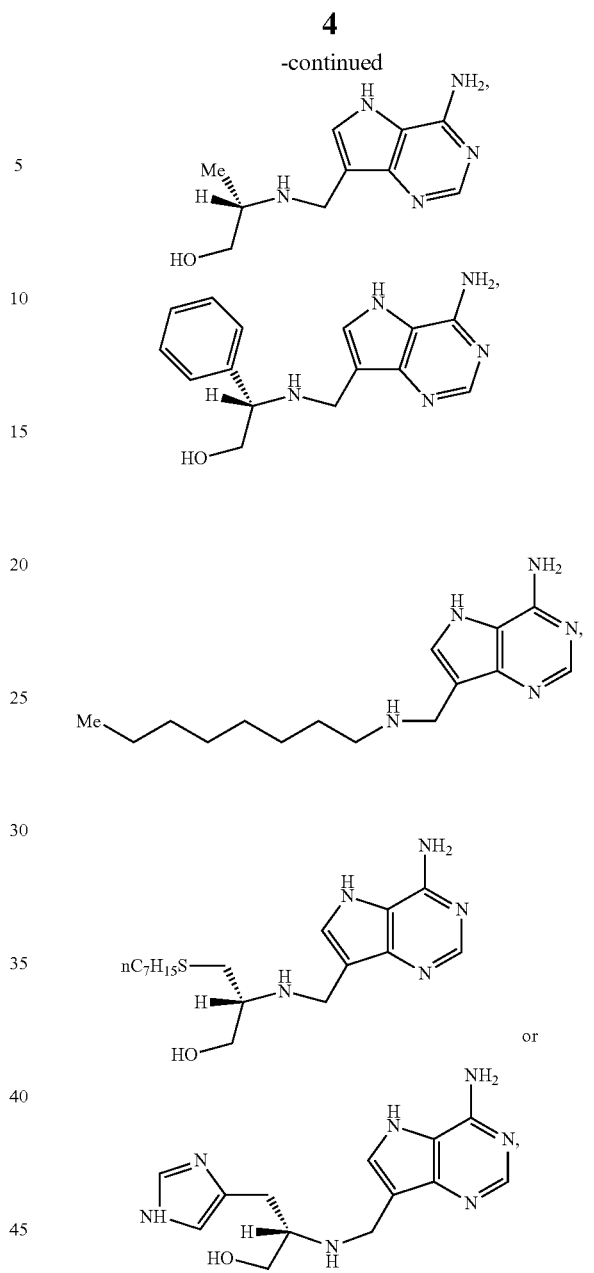

or a pharmaceutically acceptable salt thereof, or an ester thereof.

BRIEF DESCRIPTION OF THE DRAWINGS

FIG. 1. Concentration of Hexyl-SerMe-Immucillin A in mouse gastric mucin versus time following a single dose of 10 mg/kg PO.

DETAILED DESCRIPTION OF THE INVENTION

The invention provides a method of treating a *Helicobacter pylori* (*H. pylori*) infection in a subject comprising administering to the subject a compound of formula (I) in an amount effective to inhibit growth of *H. pylori*, wherein formula (I) is

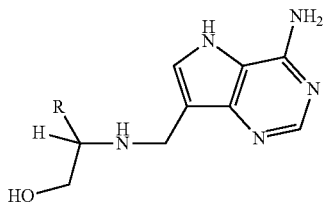
(I)

wherein R is Q or CH$_2$SQ, wherein Q is C1-C9 alkyl, aryl, heteroaryl, aralkyl, or C4-C7 cycloalkyl, and wherein Q is optionally substituted with one or more halogen, OH and/or NH$_2$ groups, or a pharmaceutically acceptable salt thereof, or an ester thereof.

Preferred compounds include those having the formula

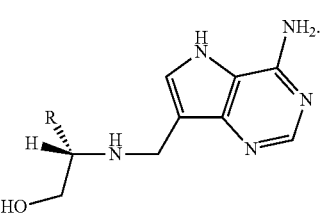

Q can be, for example, C1-C9 alkyl; e.g., C1-C5 alkyl; e.g., a methyl (Me), ethyl (Et), propyl (Pr), butyl or pentyl group. Q can be, for example, C4-C7 cycloalkyl, i.e., C4 cycloalkyl, C5 cycloalkyl, C6 cycloalkyl, or C7 cycloalkyl. Q can be, for example, aryl. The term "aryl" means an aromatic radical having 4 to 12 carbon atoms. Examples include phenyl, 1-naphthyl and 2-naphthyl. "Heteroaryl" means a 4 to 12 member ring that includes one or more N, S, or O atoms in the ring. Examples include imidazol-4-yl, imidazol-2-yl, thiazol-2-yl, thiazol-4-yl, thiazol-5-yl, pyridin-2-yl, pyridine-3-yl, pyridine-4-yl and pyrazin-2-yl. Preferred aryls and heteroaryls include those having 5 or 6 members in the ring. Preferably, the aralkyl includes a C1-C3 alkyl group and a 4-6 membered ring, which can include heteroatoms.

Q can be substituted with one or more halogen, hydroxyl or NH$_2$ groups. Preferred halogens are Cl, F, Br or I. Chlorine and fluorine are more preferred halogens. The substitution can be at an ortho, meta or para position.

Preferred compounds include those where R is Q or CH$_2$SQ, wherein Q is C2-C9 linear alkyl, aryl, heteroaryl, aralkyl, or C4-C7 cycloalkyl, and wherein Q is optionally substituted with one or more halogen, OH and/or NH$_2$ groups. Preferred compounds also include those where Q is C3-C9 linear alkyl or heteroaryl.

Preferred compounds include those selected from the group consisting of

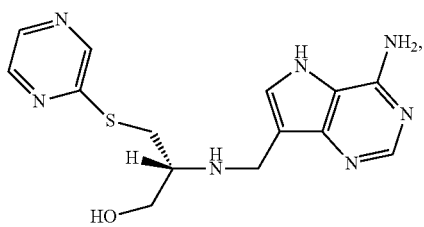

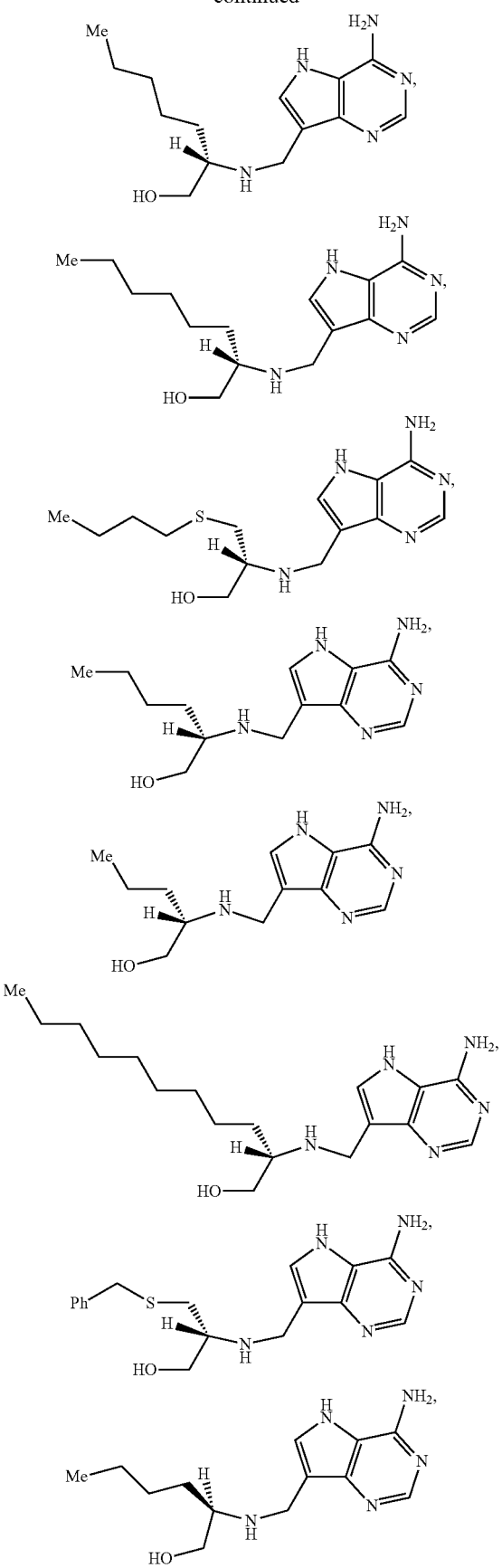

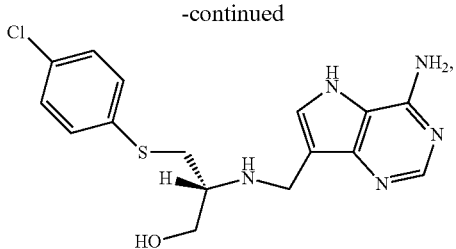
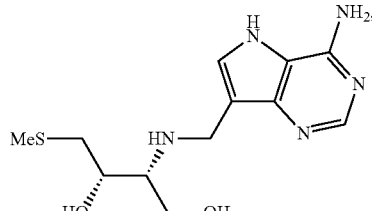
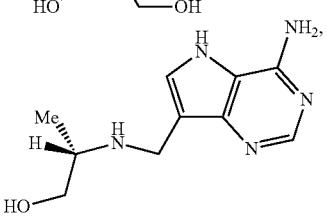
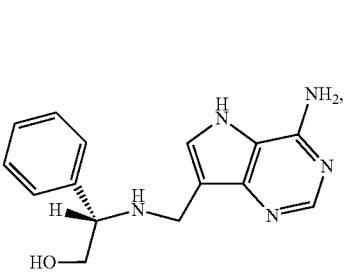
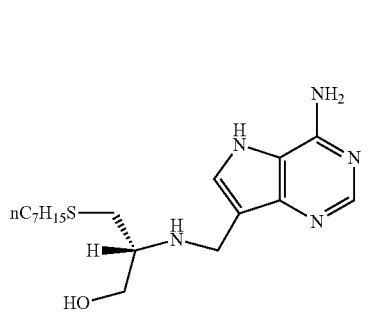
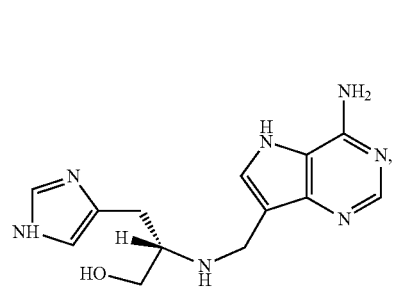 [SMILES: Nc1ncnc2c(CN[C@H](CO)Cc3c[nH]cn3)c[nH]c12]
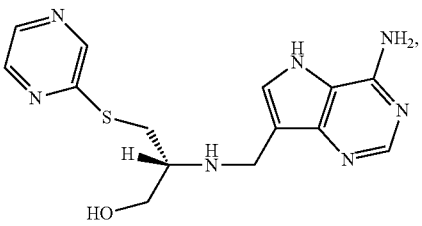
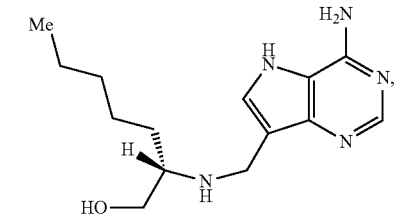
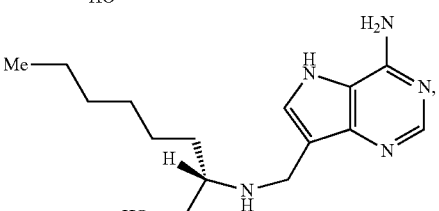
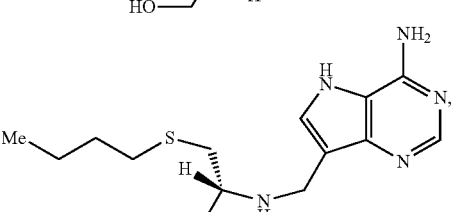
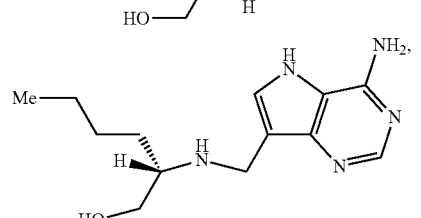
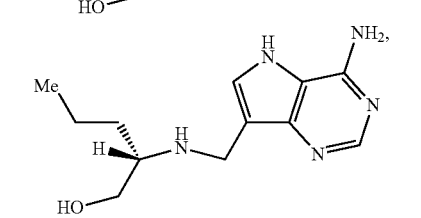
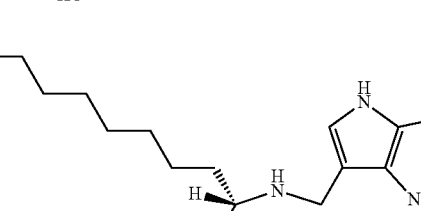
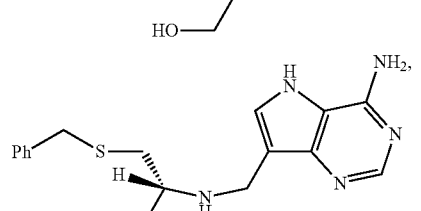
and
or a pharmaceutically acceptable salt thereof, or an ester thereof.
Accordingly, the invention provides a method of treating a *Helicobacter pylori* (*H. pylori*) infection in a subject comprising administering to the subject a compound in an amount effective to inhibit growth of *H. pylori*, wherein the compound is selected from the group consisting of:

-continued
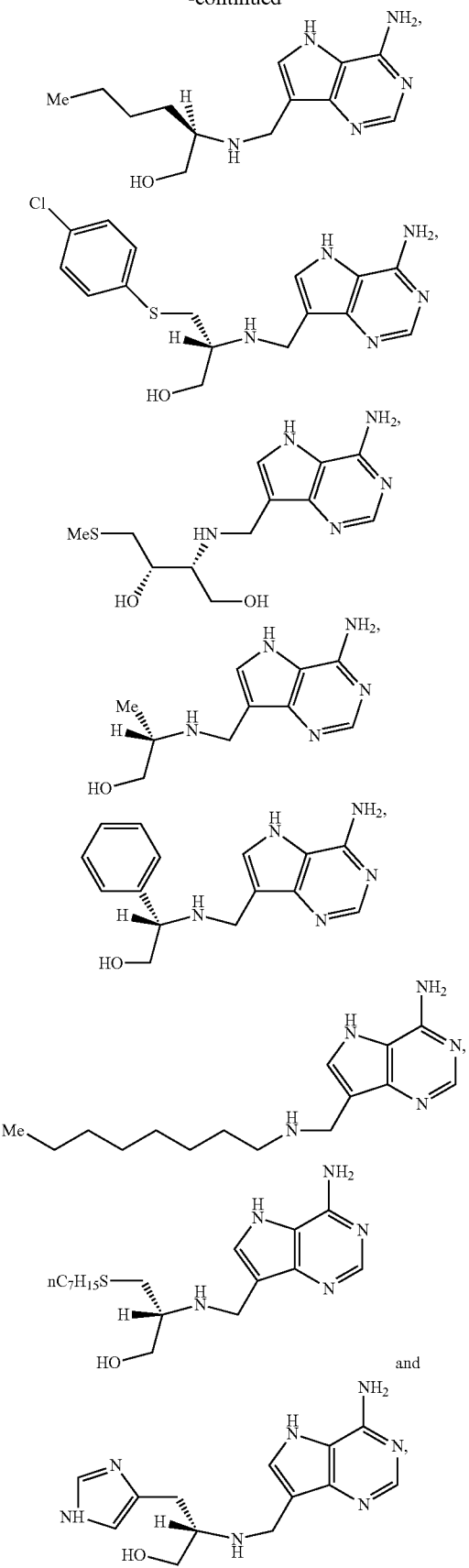
or a pharmaceutically acceptable salt thereof, or an ester thereof.
The invention further provides a compound having the structure:
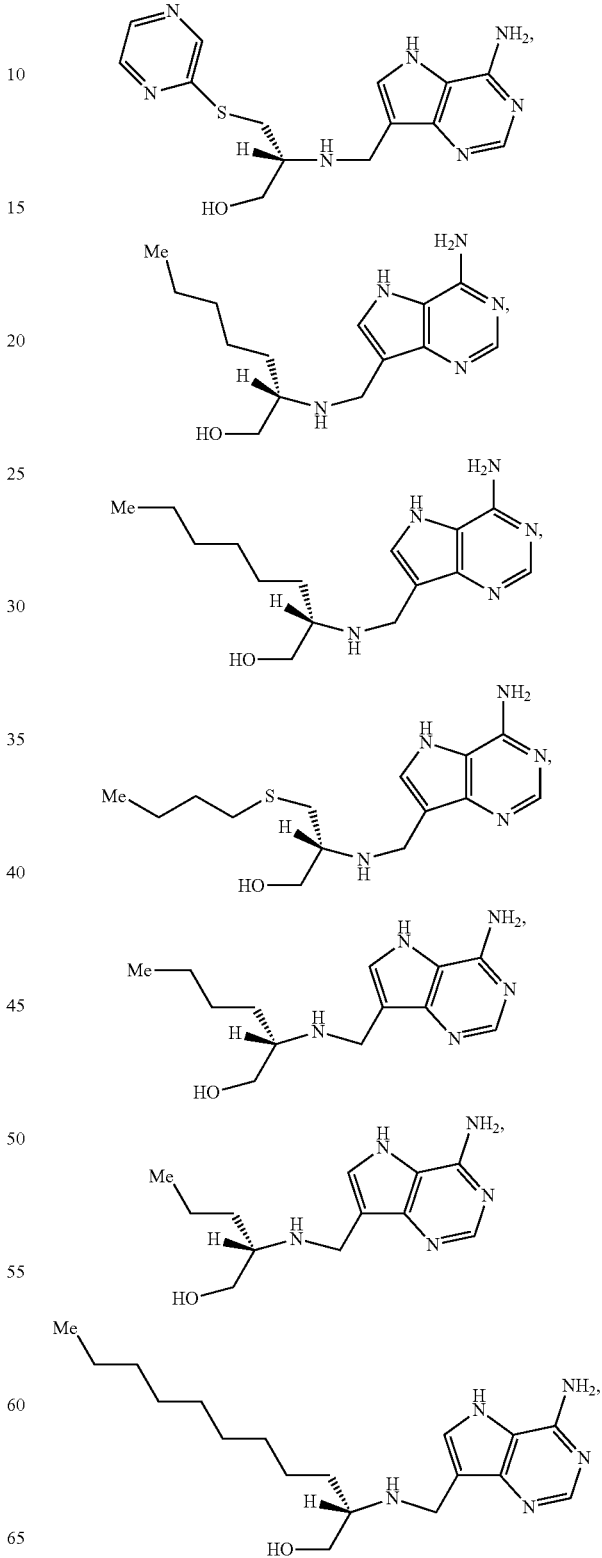

-continued

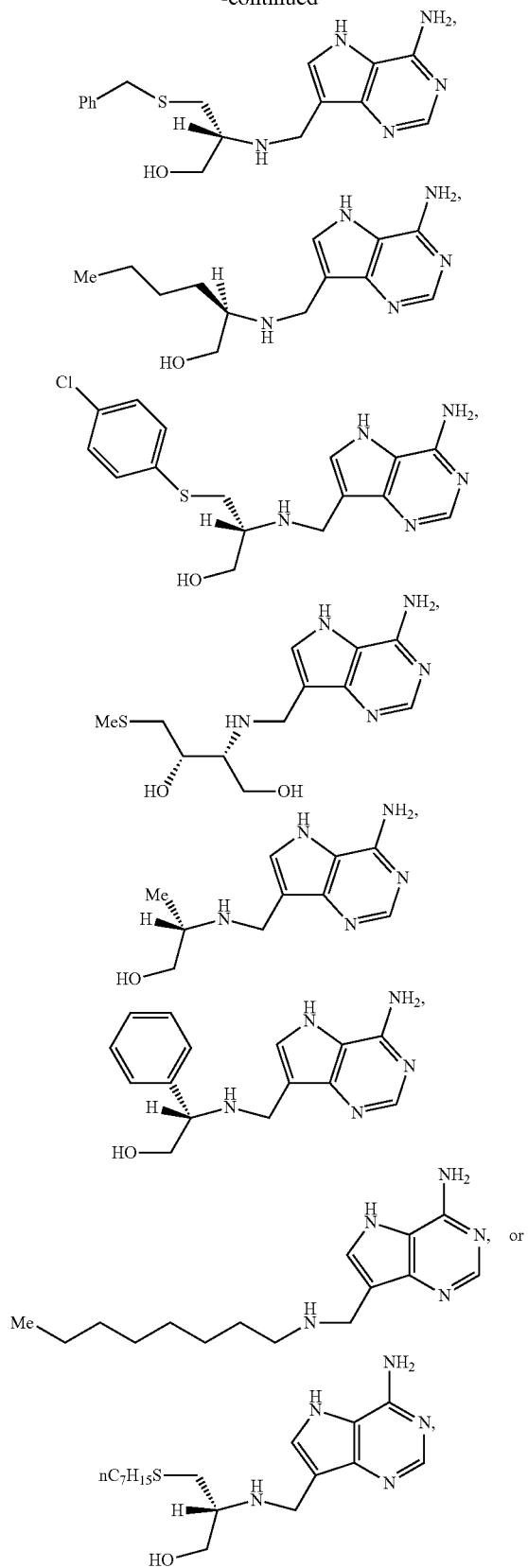

or a pharmaceutically acceptable salt thereof, or an ester thereof.

The term "pharmaceutically acceptable salts" includes non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

Preferably, the compound is administered in an amount that is effective to inhibit *H. pylori* 5'-methylthioadenosine nucleosidase (MTAN).

Preferably, the compound inhibits growth of *H. pylori* but does not inhibit the growth of one or more bacterium selected from the group consisting of *E. coli*, *V. cholerae*, *S. aureus*, *K. pneumoniae*, *S. flexneri*, *S. enterica* and *P. aeruginosa*. More preferably, the compound does not inhibit the growth of all of *E. coli*, *V. cholerae*, *S. aureus*, *K. pneumoniae*, *S. flexneri*, *S. enterica* and *P. aeruginosa*. Preferably, the compound is more effective in inhibiting growth of *H. pylori* than is amoxicillin, metronidazole or tetracyclin.

Preferably, the subject has a peptic ulcer, such as a gastric ulcer or a duodenal ulcer.

Preferably, the compound is administered orally. For oral administration, the compound can be formulated into solid or liquid preparations, for example tablets, capsules, powders, solutions, suspensions and dispersions. The compound can be formulated with agents such as, e.g., lactose, sucrose, corn starch, gelatin, potato starch, alginic acid and/or magnesium stearate.

The compound can also be administered to a subject by other routes known in the art, such as, e.g., parenterally, by inhalation, topically, rectally, nasally, buccally or via an implanted reservoir. The compound can be administered by means of sustained release.

The invention further provides for the use a compound that inhibits *Helicobacter pylori* (*H. pylori*) MTAN for the preparation of a medicament for treating a *H. pylori* infection. The invention still further provides a compound that inhibits *Helicobacter pylori* (*H. pylori*) MTAN for use for treating a *H. pylori* infection.

The invention further provides for the use a compound that inhibits *Helicobacter pylori* (*H. pylori*) MTAN for the preparation of a medicament for treating a peptic ulcer. The invention still further provides a compound that inhibits *Helicobacter pylori* (*H. pylori*) MTAN for use for treating a peptic ulcer.

The present methods can also be applied to treating infections due to other *Helicobacter* species and to *Campylobacter* species, such as *C. jejuni*.

The invention further provides a pharmaceutical composition comprising any of the compounds disclosed herein and a pharmaceutically acceptable carrier. As used herein, a "pharmaceutically acceptable carrier" is (i) compatible with the other ingredients of the composition without rendering the composition unsuitable for its intended purpose, and (ii) suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include any of the standard pharmaceutical carriers such as phosphate buffered saline solutions, water, and emulsions such as oil/water emulsions and microemulsions.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

Example 1

Materials and Methods

Materials. *H. pylori* (J99 and 43504), *K. pneumoniae*, *S. flexneri*, *S. enterica*, *S. aureus* and *P. aeruginosa* were purchased from the American Type Culture Collection. Defibrinated horse blood (DHB) was from Hemostat Laboratories (Dixon, Calif.). Tryptic soy agar (TSA) was purchased from Becton Dickinson and Company (Sparks, Md.). MacConkey agar was from Oxoid LTD. (Basingstoke, Hampshire, England). Xanthine oxidase and 5'-methylthioadenosine were purchased from Sigma-Aldrich (St Louis, Mo.). The rest of the materials were purchased with the highest purity available.

HpMTAN purification. The purification procedure of HpMTAN was described previously[10]. Briefly, BL21 (DE3) cells harboring a plasmid encoding HpMTAN with an N-terminal His6-tag were grown to an optical density of 0.7 measured at 595 nm and IPTG was introduced to a final concentration of 0.5 mM. After another 15 h at 22° C., cells were collected by centrifugation. The pellet was suspended and later disrupted by pressure cell and sonication. The soluble portion was applied to a Ni-NTA column and HpMTAN was eluted with an imidazole concentration gradient of 200 to 500 mM. The protein was desalted using a Superdex G15 gel-filtration column then equilibrated and concentrated in 10 mM Hepes, 30 mM KCl, pH 7.6. The purity was confirmed by SDS-PAGE.

$K_i$ determination. Kinetics of HpMTAN were determined using a direct assay involving absorbance decrease at 274 nm continuously as a consequence of formation of free adenine from 5'-methylthioadenosine. The $K_i$ and $K_i^*$ values were determined using coupled assays, in which xanthine oxidase was used as the coupling enzyme and absorbance increase was followed at 292 nm as the product adenine is converted to 2,8-dihydroxyadenine. Both assays have been previously described[8].

Bacterial Growth. *H. pylori* were grown for 72 hours under microaerophilic condition (5% $O_2$, 10% $CO_2$ and 85% $N_2$) at 37° C. on tryptic soy agar with 5% horse blood. To determine the MIC values, the test substance was added to the gel solution right before pouring. To compare the zones of inhibition, specific antibiotics were added to the center of disc after spreading *H. pylori*, and then *H. pylori* was allowed to grow for 72 hours under microaerophilic condition at 37° C.

General Experimental for Compounds. All reactions were performed under an argon atmosphere. Organic solutions were dried over anhydrous $MgSO_4$ and the solvents were evaporated under reduced pressure. Anhydrous and chromatography solvents were obtained commercially and used without any further purification. Potassium tert-butoxide was sublimed at 220° C./0.1 torr. Thin layer chromatography (TLC) was performed on glass or aluminum sheets coated with 60 $F_{254}$ silica gel. Organic compounds were visualized under UV light and/or a dip of 0.1% ninhydrin in EtOH, Ehrlich's solution or ammonium molybdate (5 mass %) and cerium(IV) sulfate 4 $H_2O$ (0.2 mass %) in aq. $H_2SO_4$ (2 M). Chromatography (flash column or an automated system with continuous gradient facility) was performed on silica gel (40-63 μm). Optical rotations were recorded at a path length of 1 dm and are in units of $10^{-1}$ deg $cm^2$ $g^{-1}$; concentrations are in g/100 mL. $^1H$ NMR spectra were measured in $CDCl_3$ or $CD_3OD$ (internal $Me_4Si$, δ0) and $^{13}C$ NMR spectra in $CDCl_3$ (center line as stated) or $CD_3OD$ (center line as stated). Assignments of $^1H$ and $^{13}C$ resonances were based on 2D ($^1H$-$^1H$ DQF-COSY, $^1H$-$^{13}C$ HSQC) and DEPT experiments. Abbreviations used: s, singlet, d, doublet, t, triplet, q, quartet, bs, broad singlet, bt, broad triplet, dd, doublet of doublets, ddd, doublet of doublets of doublets, dt, doublet of triplets. High resolution electrospray mass spectra (ESI-HRMS) were recorded on a Q-TOF Tandem Mass Spectrometer.

Example A

Synthesis of 2-[({4-amino-5H-pyrrolo[3,2-d]pyrimidin-7-yl}methyl)amino]ethan-1-ol (A.1)

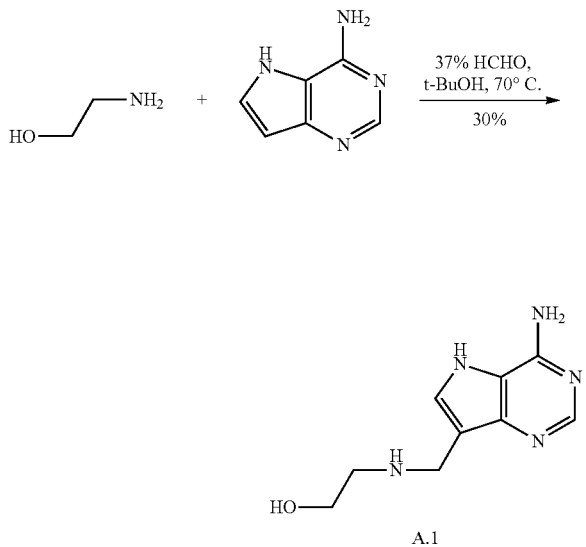

2-[({4-Amino-5H-pyrrolo[3,2-d]pyrimidin-7-yl}methyl) amino]ethan-1-ol (A.1). 2-Aminoethanol (0.099 mL, 1.64 mmol), 9-deazaadenine (0.220 g, 1.64 mmol) and aq. formaldehyde solution (37%, 0.15 mL, 1.99 mmol) were stirred together in tert-butanol (3 mL) at 70° C. for 16 h. Silica gel was added to absorb all the solvent then the solvent was evaporated and the residue purified by chromatography on silica gel ($CHCl_3$-MeOH-28% aq.$NH_4OH$, 70:25:5). Fractions containing product were evaporated and the residue chromatographed again on silica gel (2-PrOH-28% aq. $NH_4OH$, 92:8) to give A.1 as a colourless solid (0.101 g, 30%). $^1H$ NMR (500 MHz, $CD_3OD$): δ 8.16 (s, 1H), 7.47 (s, 1H), 3.95 (s, 2H), 3.68 (t, J=5.6 Hz, 2H), 2.78 (t, J=5.6 Hz, 2H). $^{13}C$ NMR (125.7 MHz, $CD_3OD$, centre line δ 49.0): δ 152.1 (C), 150.9 (CH), 146.6 (C), 129.0 (CH), 115.4 (C), 114.4 (C), 61.6 ($CH_2$), 51.6 ($CH_2$), 43.4 ($CH_2$). ESI-HRMS calcd for $C_9H_{14}N_5O^+$, $(M+H)^+$, 208.1193. found 208.1192.

Example B

Synthesis of (2S)-2-[({4-amino-5H-pyrrolo[3,2-d]pyrimidin-7-yl}methyl)amino]propan-1-ol (B.1)

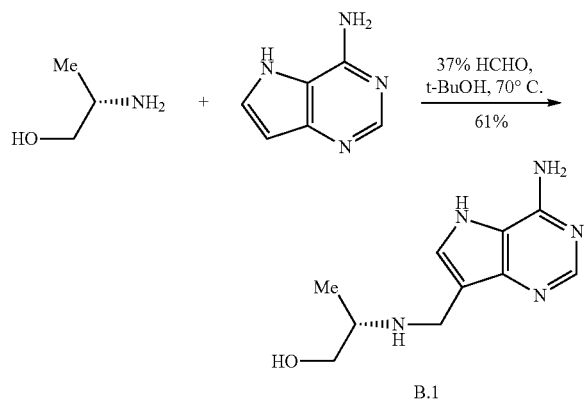

B.1

(2S)-2-[({4-Amino-5H-pyrrolo[3,2-d]pyrimidin-7-yl}methyl)amino]propan-1-ol (B.1). (2S)-2-Aminopropan-1-ol (0.120 g, 1.60 mmol), 9-deazaadenine (0.179 g, 1.33 mmol) and aq. formaldehyde solution (37%, 0.12 mL, 1.60 mmol) were stirred together in tert-butanol (3 mL) at 70° C. for 16 h. Silica gel was added to absorb all the solvent then the solvent was evaporated and the residue purified by chromatography on silica gel (CHCl$_3$-MeOH-28% aq.NH$_4$OH, 80:18.5:1.5) to afford B.1 as a colourless solid (0.180 g, 61%). $^1$H NMR (500 MHz, CD$_3$OD): δ 8.16 (s, 1H), 7.47 (s, 1H), 4.01 (d, J=13.6 Hz, 1H), 3.92 (d, J=13.6 Hz, 1H), 3.54 (dd, J=11.0, 4.8 Hz, 1H), 3.43 (dd, J=11.0, 7.0 Hz, 1H), 2.84 (m, 1H), 1.09 (d, J=6.5 Hz, 3H). $^{13}$C NMR (125.7 MHz, CD$_3$OD, centre line δ 49.0): δ 152.1 (C), 150.9 (CH), 146.5 (C), 128.9 (CH), 115.4 (C), 114.5 (C), 66.6 (CH$_2$), 54.8 (CH), 41.0 (CH$_2$), 16.5 (CH$_3$). ESI-HRMS calcd for C$_{10}$H$_{16}$N$_5$O$^+$, (M+H)$^+$, 222.1350. found, 222.1349.

Example C

Synthesis of (2S)-2-[({4-amino-5H-pyrrolo[3,2-d]pyrimidin-7-yl}methyl)amino]butan-1-ol (C.1)

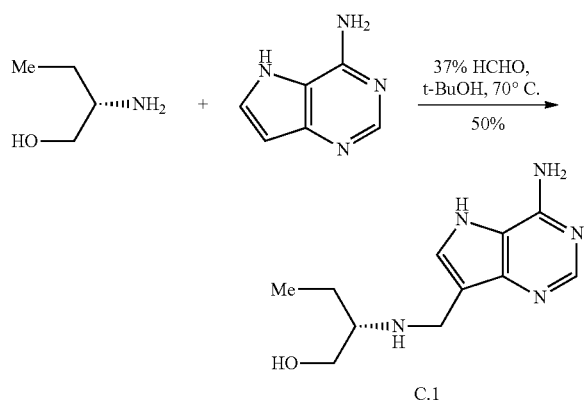

C.1

(2S)-2-[({4-Amino-5H-pyrrolo[3,2-d]pyrimidin-7-yl}methyl)amino]butan-1-ol (C.1). (2S)-2-Aminobutan-1-ol (0.100 g, 1.12 mmol), 9-deazaadenine (0.150 g, 1.12 mmol) and aq. formaldehyde solution (37%, 0.101 mL, 1.35 mmol) were stirred together in tert-butanol (3 mL) at 70° C. for 16 h. Silica gel was added to absorb all the solvent then the solvent was evaporated and the residue purified by chromatography on silica gel (CHCl$_3$-7M NH$_3$/MeOH, 9:1 then 85:15) to afford C.1 as a colourless solid (0.133 g, 50%). $^1$H NMR (500 MHz, CD$_3$OD): δ 8.16 (s, 1H), 7.47 (s, 1H), 3.99 (d, J=13.6 Hz, 1H), 3.95 (d, J=13.6 Hz, 1H), 3.67 (dd, J=11.2, 4.4 Hz, 1H), 3.48 (dd, J=11.2, 6.5 Hz, 1H), 2.61 (m, 1H), 1.62-1.53 (m, 1H), 1.51-1.42 (m, 1H), 0.91 (t, J=7.5 Hz, 3H). $^{13}$C NMR (125.7 MHz, CD$_3$OD, centre line δ 49.0): δ 152.1 (C), 150.8 (CH), 146.6 (C), 128.9 (CH), 115.4 (C), 114.8 (C), 63.9 (CH$_2$), 60.9 (CH), 41.1 (CH$_2$), 24.6 (CH$_2$), 10.7 (CH$_3$). ESI-HRMS calcd for C$_{11}$H$_{17}$N$_5$NaO$^+$, (M+Na)$^+$, 258.1326. found 258.1321.

Example D

Synthesis of (2S)-2-[({4-amino-5H-pyrrolo[3,2-d]pyrimidin-7-yl}methyl)amino]pentan-1-ol (D.1)

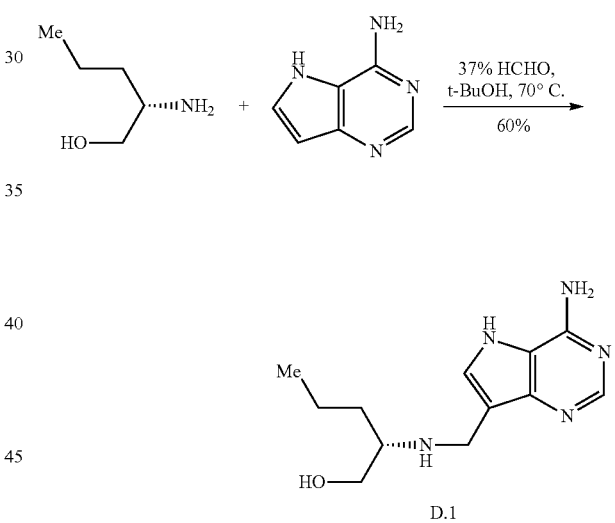

D.1

(2S)-2-[({4-Amino-5H-pyrrolo[3,2-d]pyrimidin-7-yl}methyl)amino]pentan-1-ol (D.1). (2S)-2-Aminopentan-1-ol (0.050 g, 0.48 mmol), 9-deazaadenine (0.065 g, 0.48 mmol) and aq. formaldehyde solution (37%, 0.044 mL, 0.59 mmol) were stirred in tert-butanol (2 mL) at 70° C. overnight. Silica gel was added to absorb all the solvent then the solvent was evaporated and the residue purified by chromatography on silica gel (CHCl$_3$-7M NH$_3$/MeOH, 9:1 then 85:15) to afford D.1 as a colourless solid (0.073 g, 60%). $^1$H NMR (500 MHz, CD$_3$OD): δ 8.16 (s, 1H), 7.47 (s, 1H), 3.99 (d, J=13.7 Hz, 1H), 3.96 (d, J=13.7 Hz, 1H), 3.66 (dd, J=11.3, 4.4 Hz, 1H), 3.48 (dd, J=11.3, 6.6 Hz, 1H), 2.69 (m, 1H), 1.54-1.30 (m, 4H), 0.89 (t, J=7.2 Hz, 3H). $^{13}$C NMR (125.7 MHz, CD$_3$OD, centre line δ 49.0): δ 152.1 (C), 150.8 (CH), 146.6 (C), 128.9 (CH), 115.4 (C), 114.7 (C), 62.3 (CH$_2$), 59.2 (CH), 41.1 (CH$_2$), 34.3 (CH$_2$), 20.3 (CH$_2$), 14.6 (CH$_3$). ESI-HRMS calcd for C$_{12}$H$_{20}$N$_5$O$^+$, (M+H)$^+$, 250.1663. found 250.1663.

Example E. Synthesis of (2S)-2-[({4-amino-5H-pyrrolo[3,2-d]pyrimidin-7-yl}methyl)amino]hexan-1-ol (E.1)

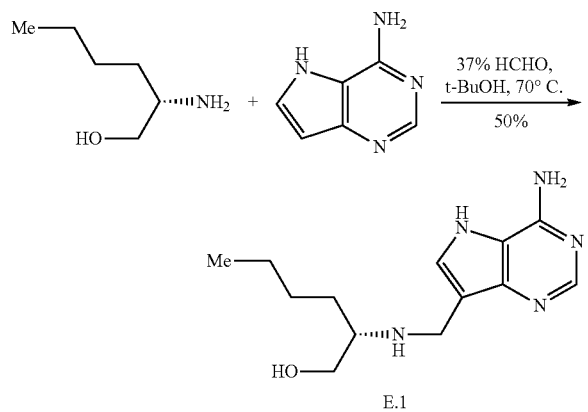

(2S)-2-[({4-Amino-5H-pyrrolo[3,2-d]pyrimidin-7-yl}methyl)amino]hexan-1-ol (E.1). (2S)-2-Aminohexan-1-ol (0.100 g, 0.85 mmol), 9-deazaadenine (0.114 g, 0.85 mmol) and aq. formaldehyde solution (37%, 0.077 mL, 1.02 mmol) were stirred together at 70° C. in tert-butanol (3 mL) for 16 h. Silica gel was added to absorb all the solvent then the solvent was evaporated and the residue purified by chromatography on silica gel (CHCl$_3$-7M NH$_3$/MeOH, 9:1 then 85:15) to afford E.1 as a colourless solid (0.112 g, 50%). $^1$H NMR (500 MHz, CD$_3$OD): δ 8.16 (s, 1H), 7.47 (s, 1H), 3.97 (s, 2H), 3.65 (dd, J=11.2, 4.4 Hz, 1H), 3.48 (dd, J=11.2, 6.6 Hz, 1H), 2.66 (m, 1H), 1.55-1.38 (m, 2H), 1.32-1.22 (m, 4H), 0.88 (t, J=7.1 Hz, 3H). $^{13}$C NMR (125.7 MHz, CD$_3$OD, centre line δ 49.0): δ 152.1 (C), 150.8 (CH), 146.6 (C), 128.9 (CH), 115.4 (C), 114.7 (C), 64.4 (CH$_2$), 59.3 (CH), 41.2 (CH$_2$), 31.7 (CH$_2$), 29.3 (CH$_2$), 23.9 (CH$_2$), 14.3 (CH$_3$). ESI-HRMS calcd for C$_{13}$H$_{21}$N$_5$NaO$^+$, (M+Na)$^+$, 286.1644. found 286.1644.

Example F

Synthesis of (2R)-2-[({4-amino-5H-pyrrolo[3,2-d]pyrimidin-7-yl}methyl)amino]hexan-1-ol (F.1)

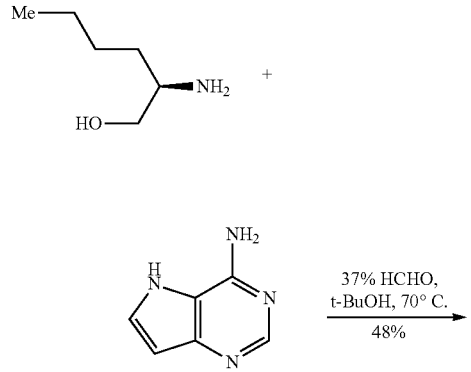

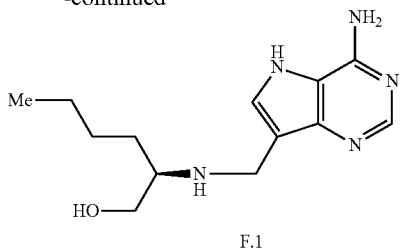

(2R)-2-[({4-Amino-5H-pyrrolo[3,2-d]pyrimidin-7-yl}methyl)amino]hexan-1-ol (F.1). (2R)-2-Aminohexan-1-ol (0.100 g, 0.85 mmol), 9-deazaadenine (0.114 g, 0.85 mmol) and aq. formaldehyde solution (37%, 0.077 mL, 1.02 mmol) were stirred together at 70° C. in tert-butanol (3 mL) for 16 h. Silica gel was added to absorb all the solvent then the solvent was evaporated and the residue purified by chromatography on silica gel (CHCl$_3$-7M NH$_3$/MeOH, 9:1 then 85:15) to afford F.1 as a colourless solid (0.108 g, 48%). The $^1$H and $^{13}$C NMR were identical to the enantiomer E.1. ESI-HRMS calcd for C$_{13}$H$_{22}$N$_5$O$^+$ (M+H)$^+$, 264.1819. found 264.1717.

Example G

Synthesis of (2S)-2-[({4-amino-5H-pyrrolo[3,2-d]pyrimidin-7-yl}methyl)amino]-3-methylbutan-1-ol (G.1)

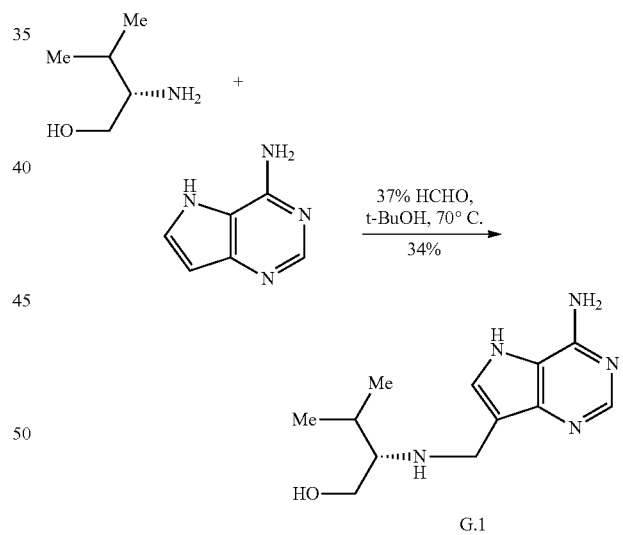

(2S)-2-[({4-Amino-5H-pyrrolo[3,2-d]pyrimidin-7-yl}methyl)amino]-3-methylbutan-1-ol (G.1). (2S)-2-Amino-3-methylbutan-1-ol (0.100 g, 0.97 mmol) 9-deazaadenine (0.130 g, 0.97 mmol), and aq. formaldehyde solution (37%, 0.087 mL, 1.16 mmol) were stirred in tert-butanol (3 mL) at 70° C. for 16 h. Silica gel was added to absorb all the solvent then the solvent was evaporated and the residue purified by chromatography on silica gel (CHCl$_3$-7M NH$_3$/MeOH, 93:7 then 85:15) to give G.1 as a colourless solid (0.082 g, 34%). $^1$H NMR (500 MHz, CD$_3$OD): δ 8.16 (s, 1H), 7.47 (s, 1H), 3.99 (d, J=13.6 Hz, 1H), 3.95 (d, J=13.6 Hz, 1H), 3.68 (dd, J=11.3, 4.8 Hz, 1H), 3.54 (dd, J=11.3, 6.5 Hz, 1H), 2.49 (m, 1H), 1.90 (m, 1H), 0.93 (d, J=6.9 Hz, 3H), 0.88 (d, J=6.9 Hz, 3H). $^{13}$C NMR (125.7 MHz, CD$_3$OD, centre line δ 49.0): δ 152.1 (C), 150.8 (CH), 146.7 (C), 129.0 (CH), 115.4 (C), 115.0 (C), 64.6 (CH$_2$), 62.3 (CH), 41.9 (CH), 29.8 (CH$_2$), 19.2 (CH$_3$), 18.9 (CH$_3$). ESI-HRMS calcd for C$_{12}$H$_{20}$N$_5$O$^+$ (M+H)$^+$, 250.1663. found 250.1661.

Example H

Synthesis of (2S)-2-[({4-amino-5H-pyrrolo[3,2-d]pyrimidin-7-yl}methyl)amino]-4-methylpentan-1-ol (H.1)

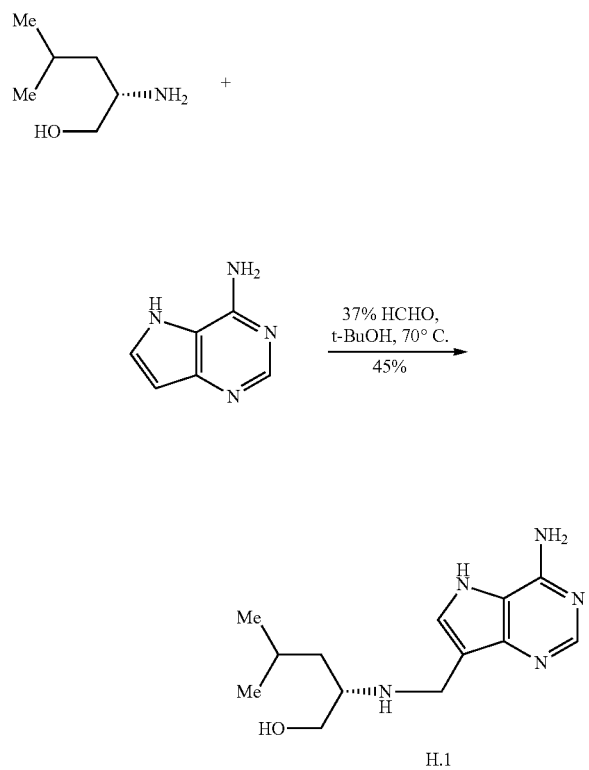

(2S)-2-[({4-Amino-5H-pyrrolo[3,2-d]pyrimidin-7-yl}methyl)amino]-4-methylpentan-1-ol (H.1). (2S)-2-Amino-4-methyl-pentan-1-ol (0.100 g, 0.85 mmol), 9-deazaadenine (0.114 g, 0.85 mmol), and aq. formaldehyde solution (37%, 0.077 mL, 1.02 mmol) were stirred in tert-butanol (3 mL) at 70° C. for 16 h. Silica gel was added to absorb all the solvent then the solvent was evaporated and the residue purified by chromatography on silica gel (CHCl$_3$-7M NH$_3$/MeOH, 93:7 then 85:15) to give H.1 as a colourless solid (0.102 g, 45%). $^1$H NMR (500 MHz, CD$_3$OD): δ 8.16 (s, 1H), 7.47 (s, 1H), 3.97 (s, 2H), 3.65 (dd, J=11.3, 4.4 Hz, 1H), 3.47 (dd, J=11.3, 6.5 Hz, 1H), 2.75 (m, 1H), 1.62 (m, 1H), 1.35 (ddd, J=13.7, 7.4, 6.2 Hz, 1H), 1.28 (ddd, J=13.9, 7.2, 7.2 Hz, 1H), 0.88 (d, J=6.6 Hz, 3H), 0.80 (d, J=6.6 Hz, 3H). $^{13}$C NMR (125.7 MHz, CD$_3$OD, centre line δ 49.0): δ 152.1 (C), 150.8 (CH), 146.6 (C), 129.0 (CH), 115.5 (C), 114.7 (C), 64.6 (CH$_2$), 57.2 (CH), 41.6 (CH$_2$), 41.0 (CH$_2$), 26.0 (CH), 23.3 (CH$_3$), 23.1 (CH$_3$). ESI-HRMS calcd for C$_{13}$H$_{22}$N$_5$O$^+$, (M+H)$^+$, 264.1819. found 264.1820.

Example I

Synthesis of (2S,3S)-2-[({4-amino-5H-pyrrolo[3,2-d]pyrimidin-7-yl}methyl)amino]-3-methylpentan-1-ol (I.1)

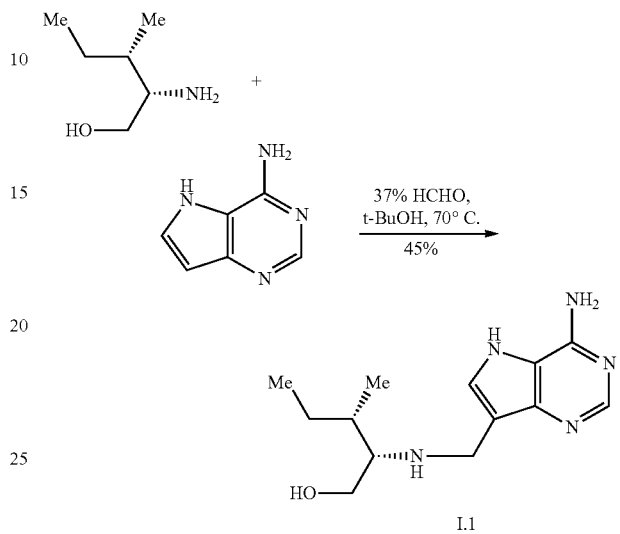

(2S,3S)-2-[({4-Amino-5H-pyrrolo[3,2-d]pyrimidin-7-yl}methyl)amino]-3-methylpentan-1-ol (I.1). (2S,3S)-2-Amino-3-methylpentan-1-ol (0.120 g, 1.02 mmol), 9-deazaadenine (0.137 g, 1.02 mmol), and aq. formaldehyde solution (37%, 0.092 mL, 1.22 mmol) were heated and stirred in tert-butanol (3 mL) at 70° C. for 16 h. Silica gel was added to absorb all the solvent then the solvent was evaporated and the residue purified by chromatography on silica gel (CHCl$_3$-7M NH$_3$/MeOH, 92:8 then 89:11 then 85:15) to afford I.1 as a colourless waxy solid (0.120 g, 45%). $^1$H NMR (500 MHz, CD$_3$OD): δ 8.16 (s, 1H), 7.47 (s, 1H), 3.98 (s, 2H), 3.69 (dd, J=11.3, 4.3 Hz, 1H), 3.51 (dd, J=11.3, 7.1 Hz, 1H), 2.62 (ddd, J=7.0, 4.4, 4.4 Hz, 1H), 1.67 (m, 1H), 1.46 (m, 1H), 1.17 (m, 1H), 0.89-0.85 (m, 6H). $^{13}$C NMR (125.7 MHz, CD$_3$OD, centre line δ 49.0): δ 152.1 (C), 150.8 (CH), 146.7 (C), 129.0 (CH), 115.4 (C), 114.9 (C), 63.1 (CH), 62.1 (CH$_2$), 41.8 (CH$_2$), 36.7 (CH), 27.2 (CH$_2$), 15.0 (CH$_3$), 12.3 (CH$_3$). ESI-HRMS calcd for C$_{13}$H$_{22}$N$_5$O$^+$, (M+H)$^+$, 264.1819. found 264.1820.

Example J

Synthesis of (2S)-2-[({4-amino-5H-pyrrolo[3,2-d]pyrimidin-7-yl}methyl)amino]-2-phenylethan-1-ol (J.1)

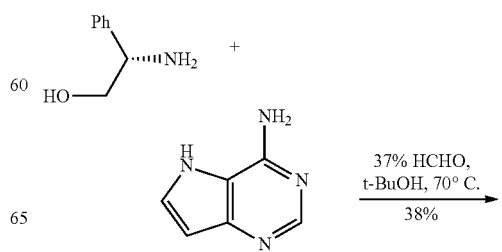

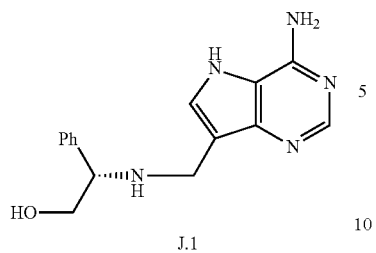

J.1

(2S)-2-[({4-Amino-5H-pyrrolo[3,2-d]pyrimidin-7-yl}methyl)amino]-2-phenylethan-1-ol (J1). (2S)-2-Amino-2-phenyl-ethanol (0.150 g, 1.09 mmol) 9-deazaadenine (0.147 g, 1.10 mmol), and aq. formaldehyde solution (37%, 0.098 mL, 1.31 mmol) were stirred and heated in tert-butanol (3 mL) at 70° C. for 16 h. Silica gel was added to absorb all the solvent then the solvent was evaporated and the residue purified by chromatography on silica gel (CHCl$_3$-7M NH$_3$/MeOH, 92:8 then 89:11 then 85:15) to afford J.1 as a colourless foam (0.117 g, 38%). $^1$H NMR (500 MHz, CD$_3$OD): δ 8.14 (s, 1H), 7.38-7.31 (m, 5H), 7.28-7.24 (m, 1H), 3.88-3.82 (m, 2H), 3.75 (d, J=13.8 Hz, 1H), 3.65 (dd, J=11.0, 4.9 Hz, 1H), 3.60 (dd, J=11.0, 8.4 Hz, 1H). $^{13}$C NMR (125.7 MHz, CD$_3$OD, centre line δ 49.0): δ 152.0 (C), 150.8 (CH), 146.6 (C), 141.5 (C), 129.6 (CH), 129.0 (CH), 128.8 (CH), 128.6 (CH), 115.5 (C), 114.7 (C), 67.7 (CH$_2$), 65.4 (CH), 41.7 (CH$_2$). ESI-HRMS calcd for C$_{15}$H$_{18}$N$_5$O$^+$, (M+H)$^+$, 284.1506. found 284.1501.

Example K

Synthesis of (2R)-2-[({4-amino-5H-pyrrolo[3,2-d]pyrimidin-7-yl}methyl)amino]-3-[(4-chlorophenyl)sulfanyl]propan-1-ol (K.3)

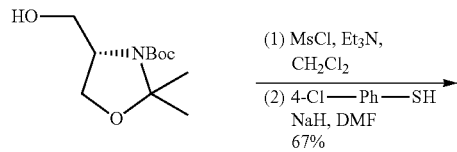

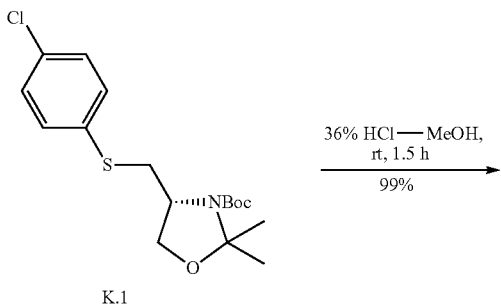

K.1

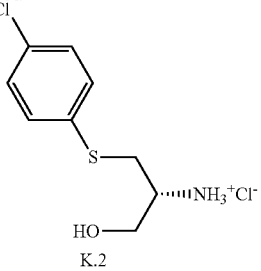

K.2

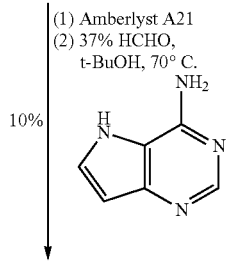

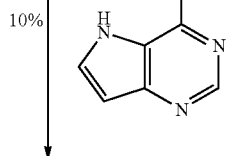

K.3 tert-Butyl (4R)-4-{[(4-chlorophenyl)sulfanyl]methyl}-2,2-dimethyl-1,3-oxazolidine-3-carboxylate (K.1) . Methanesulfonyl chloride (0.40 ml, 5.19 mmol) was added dropwise to a stirred solution of tert-butyl (4S)-4-(hydroxymethyl)-2,2-dimethyl-1,3-oxazolidine-3-carboxylate [prepared as for its enantiomer, Dondoni, et al.[13]] (1.00 g, 4.32 mmol) and triethylamine (1.22 ml, 8.65 mmol) in CH$_2$Cl$_2$ (15 mL) at 0° C. The mixture was warmed to rt and stirred for 20 min then washed with sat NaHCO$_3$ (3×5 mL), dried, and the solvent evaporated to give the crude mesylate as an oil (1.22 g, 3.94 mmol).

Step 2. 4-chlorobenzene-1-thiol (0.351 g, 2.42 mmol) was added to a solution of sodium hydride (60%, 0.089 g, 2.23 mmol) in DMF (3 mL) at 0° C. After 20 min a solution of the mesylate from step 1 above (0.30 g, 0.97 mmol) in DMF (0.75 ml) was added and the mixture warmed to rt and stirred for 16 h. Water (2 mL) was added and the mixture extracted with Et$_2$O (60 mL). The extract was washed with H$_2$O (3×5 mL), brine (5 mL), dried and the solvent evaporated to a colourless oil that was chromatographed on silica gel (gradient of 0-6% EtOAc in hexanes) to give K.1 as a colourless gum (0.234 g, 67%). [α]$_D^{20}$ −17.9 (c 1.05, CHCl$_3$). $^1$H NMR (500 MHz, CDCl$_3$): δ 7.40-7.30 (m, 2H), 7.28-7.22 (m, 2H), 4.11-3.98 (m, 1.5H), 3.94-3.89 (m, 1.5H), 3.50 (d, J=13.7 Hz, 0.5H), 3.27 (d, J=13.4 Hz, 0.5H), 2.79 (dd, J=13.5, 10.7 Hz, 1H), 1.63-1.56 (m, 3H), 1.51-1.42 (m, 12H). $^{13}$C NMR (125.7 MHz, CDCl$_3$, centre line δ 77.0): δ 152.1, 151.4 (C), 134.2, 133.8 (C), 132.5, 131.6 (C), 130.9, 129.3 (CH), 129.1 (CH), 94.5, 93.9 (C), 80.5, 80.3 (C), 66.0 (CH$_2$), 56.6, 56.3 (CH), 35.7, 33.8 (CH$_2$), 28.5, 28.4 (CH$_3$), 27.7, 27.0 (CH$_3$), 24.3, 23.1 (CH$_3$). ESI-HRMS calcd for C$_{17}$H$_{24}^{35}$ClNNaO$_3$S$^+$, (M+Na)$^+$, 380.1058. found 380.1056.

(2R)-2-Amino-3-[(4-chlorophenyl)sulfanyl]propan-1-ol hydrochloride (K.2). Compound K.1 (0.228 g, 0.64 mmol) was dissolved in MeOH (3 mL), cooled to 0° C. and aq. hydrochloric acid (36%, 2 mL) added. The mixture was stirred at rt for 16 h, then the solvent was evaporated to give K.2 as a colourless solid (0.161 g, 99%). $[\alpha]_D^{20}$ −27.7 (c 1.09, MeOH). $^1$H NMR (500 MHz, CD$_3$OD): δ 7.47 (d, J=8.6 Hz, 2H), 7.36 (d, J=8.7 Hz, 2H), 3.82 (dd, J=11.7, 3.4 Hz, 1H), 3.74 (dd, J=11.7, 5.0 Hz, 1H), 3.30-3.25 (m, 2H), 3.19 (dd. J=16.3, 9.2 Hz, 1H). $^{13}$C NMR (125.7 MHz, CD$_3$OD, centre line δ 49.0): δ 134.31 (C), 134.26 (C), 132.9 (CH), 130.5 (CH), 61.2 (CH$_2$), 53.5 (CH), 34.1 (CH$_2$). ESI-HRMS calcd for C$_9$H$_{13}$$^{35}$ClNOS$^+$, (M−HCl+H)$^+$, 218.0401. found 218.0408.

(2R)-2-[({4-Amino-5H-pyrrolo[3,2-d]pyrimidin-7-yl}methyl)amino]-3-[(4-chlorophenyl)sulfanyl]propan-1-ol (K.3). Compound K.2 (0.151 g, 0.59 mmol) was dissolved in MeOH (10 mL) and neutralized with Amberlyst A21 resin. The mixture was then passed through a short column of the same resin and eluted with MeOH to give the free amino form of K.2 as a yellow oil (129 mg). This was dissolved in tert-butanol (3 mL) then aq. formaldehyde solution (37%, 0.060 mL, 0.80 mmol) and 9-deazaadenine (0.080 g, 0.60 mmol) were added and the mixture stirred at 70° C. for 16 h. Silica gel was added to absorb all the solvent then the solvent was evaporated and the residue purified by chromatography on silica gel (CHCl$_3$-7M NH$_3$/MeOH, 92:8 then 85:15) and the fractions containing the product were evaporated. The residue was further purified on silica gel (CHCl$_3$-MeOH-28% aq. NH$_4$OH, 92:8:0.5) to give K.3 as a colourless foam (0.022 g, 10%). $^1$H NMR (500 MHz, CD$_3$OD): δ 8.16 (s, 1H), 7.35 (s, 1H), 7.13-7.08 (m, 4H), 4.02 (d, J=14.0 Hz, 1H), 3.92 (d, J=14.0 Hz, 1H), 3.70 (dd, J=11.3, 5.2 Hz, 1H), 3.66 (dd, J=11.3, 5.2 Hz, 1H), 3.13 (dd, J=13.8, 6.2 Hz, 1H), 2.92 (dd, J=13.8, 6.9 Hz, 1H), 2.75 (m, 1H). $^{13}$C NMR (125.7 MHz, CD$_3$OD, centre line δ 49.0): δ 152.0 (C), 150.8 (CH), 146.5 (C), 135.8 (C), 133.0 (C), 131.8 (CH), 129.8 (CH), 129.1 (CH), 115.5 (C), 114.4 (C), 63.5 (CH$_2$), 57.0 (CH), 41.0 (CH$_2$), 36.1 (CH$_2$). ESI-HRMS calcd for C$_{16}$H$_{18}$$^{35}$ClN$_5$NaOS$^+$ (M+Na)$^+$, 386.0813. found 386.0816.

Example L

Synthesis of (2R)-2-[({4-amino-5H-pyrrolo[3,2-d]pyrimidin-7-yl}methyl)amino]-3-(benzylsulfanyl)propan-1-ol (L.3)

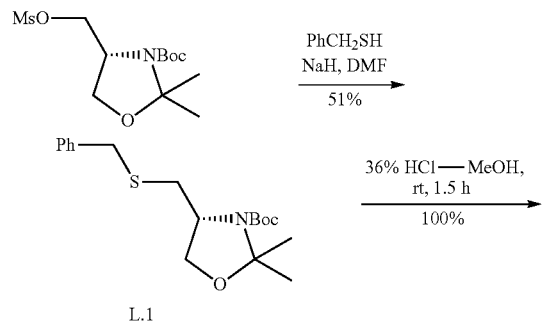

tert-Butyl (4R)-4-[(benzylsulfanyl)methyl]-2,2-dimethyl-1,3-oxazolidine-3-carboxylate (L.1). Phenylmethanethiol (0.285 ml, 2.42 mmol) was added to a stirred solution of sodium hydride (60%, 0.089 g, 2.23 mmol) in DMF (3 mL) at 0° C. After 20 min a solution of the crude mesylate (0.3 g, 0.97 mmol, from step 1 of the preparation of K.1) in DMF (0.75 ml) was added then the mixture was warmed to rt and stirred for 16 h. Water (2 ml) was added and the mixture extracted with Et$_2$O (60 mL). The extract was washed with H$_2$O (3×5 mL), brine (5 mL), dried and the solvent evaporated to a colourless oil that was chromatographed on silica gel (gradient of 0-6% EtOAc in hexanes) to give L.1 as a colourless gum (0.166 g, 51%). $[\alpha]_D^{20}$ +61.7 (c 1.12, CHCl$_3$). $^1$H NMR (500 MHz, CDCl$_3$): δ 7.40-7.28 (m, 4H), 7.26-7.20 (m, 1H), 4.09 (d, J=7.1 Hz, 0.5H), 3.99-3.85 (m, 2.5H). 3.76 (s, 2H), 2.86 (m, 1H), 2.51 (q, J=13.0 Hz, 1H), 1.58, 1.53, 1.49, 1.47, 1.46, 1.42 (6×s, 15H). $^{13}$C NMR (125.7 MHz, CDCl$_3$, centre line δ 77.0): δ 152.0, 151.4 (C), 138.5, 138.1 (C), 129.0, 128.7 (CH), 128.6, 128.4 (CH), 127.2, 126.9 (CH), 94.2, 93.7 (C), 80.3, 79.9 (C), 66.5 (CH$_2$), 57.2, 56.9 (CH), 36.9, 36.4 (CH$_2$), 34.8, 33.6 (CH$_2$), 28.4 (CH$_3$), 27.6, 26.8 (CH$_3$), 24.4, 23.2 (CH$_3$). ESI-HRMS calcd for C$_{18}$H$_{27}$$^{35}$ClNNaO$_3$S$^+$ (M+Na)$^+$, 360.1604. found 360.1592.

(2R)-2-Amino-3-(benzylsulfanyl)propan-1-ol hydrochloride (L.2). Compound L.1 (0.166 g, 0.49 mmol) was dissolved in MeOH (3 mL), cooled to 0° C. and aq. hydrochloric acid (36%, 2 mL) added. After stirring at rt for 1.5 h, the solvent was evaporated to a colourless gum that scratched down to a colourless solid (0.115 g, 100%). $[\alpha]_D^{20}$ −52.6 (c 0.91, MeOH). $^1$H NMR (500 MHz, CD$_3$OD): δ 7.38-7.35 (m, 2H), 7.34-7.30 (m, 2H), 7.25 (m, 1H), 3.81 (s, 2H), 3.77 (dd, J=11.7, 3.8 Hz, 1H), 3.65 (dd, J=11.7, 5.7 Hz, 1H), 3.27 (m, 1H), 2.74 (dd, J=14.2, 6.7 Hz, 1H), 2.67 (dd, J=14.2, 7.4 Hz, 1H). $^{13}$C NMR (125.7 MHz, CD$_3$OD, centre line δ 49.0): δ 139.2 (C), 130.1 (CH), 129.7 (CH), 128.3

(CH), 61.5 (CH$_2$), 53.7 (CH), 37.1 (CH$_2$), 31.2 (CH$_2$). ESI-HRMS calcd for C$_{10}$H$_{1635}$ClNOS$^+$, (M−HCl+H)$^+$, 198.0948. found 198.0948.

(2R)-2-[({4-Amino-5H-pyrrolo[3,2-d]pyrimidin-7-yl}methyl)amino]-3-(benzylsulfanyl)propan-1-ol (L.3). Compound L.2 (0.170 g, 0.73 mmol) was dissolved in MeOH (10 mL) and neutralized with Amberlyst A21 resin. The mixture was then passed through a small column of the same resin and eluted with MeOH to give the free amino form of L.2 as a yellow oil. This was dissolved in tert-butanol (3 mL) then aq. formaldehyde solution (37%, 0.071 mL, 0.95 mmol) and 9-deazaadenine (0.098 g, 0.73 mmol) added and the mixture was stirred at 70° C. for 16 h. Silica gel was added to absorb all the solvent then the solvent was evaporated and the residue purified by chromatography on silica gel (CHCl$_3$-MeOH-28% aq. NH4OH, 92:8:0.5). The fractions containing the product were evaporated and the residue was further purified on silica gel (gradient of 2-10% 7M NH$_3$/MeOH—CHCl$_3$) to give L.3 as a colourless solid (0.021 g, 8%). $^1$H NMR (500 MHz, CD$_3$OD): δ 8.17 (s, 1H), 7.43 (s, 1H), 7.25-7.21 (m, 2H), 7.19-7.15 (m, 3H), 3.99 (d, J=13.8 Hz, 1H), 3.91 (d, J=13.8 Hz, 1H), 3.66 (dd, J=11.2, 4.9 Hz, 1H), 3.57 (dd, J=11.2, 5.5 Hz, 1H), 3.53 (d, J=1.6 Hz, 2H), 2.77 (m, 1H), 2.60 (dd, J=13.6, 6.4 Hz, 1H), 2.49 (dd, J=13.6, 6.9 Hz, 1H). $^{13}$C NMR (125.7 MHz, CD$_3$OD, centre line δ 49.0): δ 152.1 (C), 150.9 (CH), 146.6 (C), 139.8 (C), 129.9 (CH), 129.4 (CH), 129.1 (CH), 127.9 (CH), 115.5 (C), 114.7 (C), 63.8 (CH$_2$), 57.8 (CH), 41.2 (CH$_2$), 36.9 (CH$_2$), 33.9 (CH$_2$). ESI-HRMS calcd for C$_{17}$H$_{21}$N$_5$NaOS$^+$ (M+Na)$^+$, 366.1360. found 366.1362.

Example P

Synthesis of (2S)-2-[({4-amino-5H-pyrrolo[3,2-d]pyrimidin-7-yl}methyl)amino]-3-(1H-imidazol-4-yl)propan-1-ol (P.4)

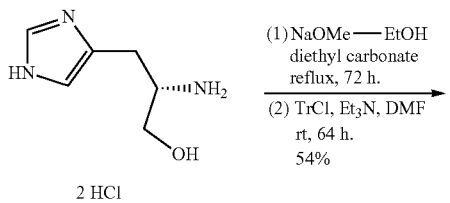

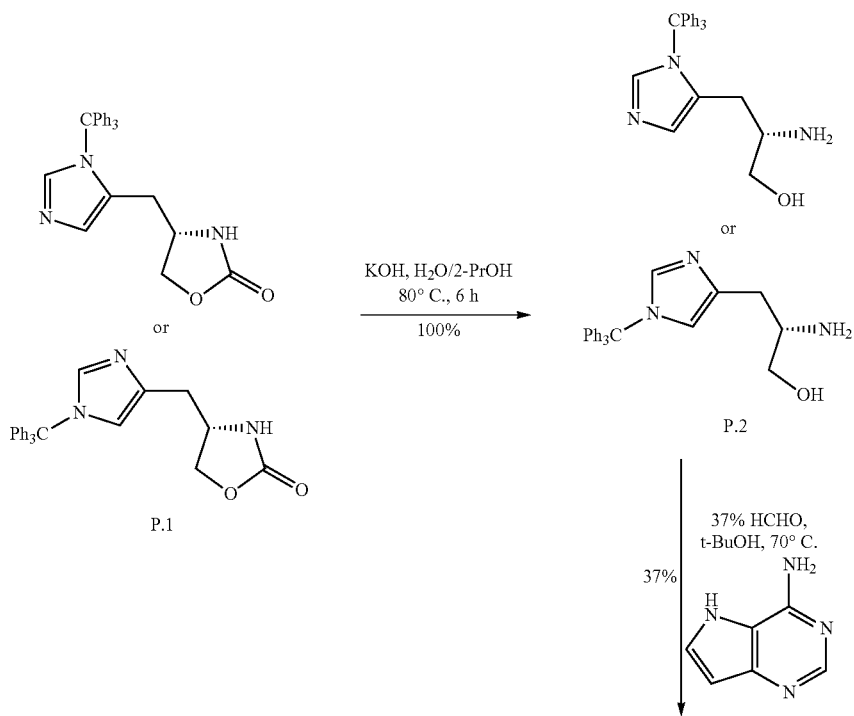

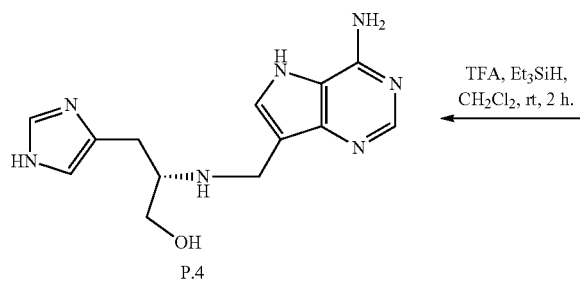

P.4

TFA, Et₃SiH, CH₂Cl₂, rt, 2 h.

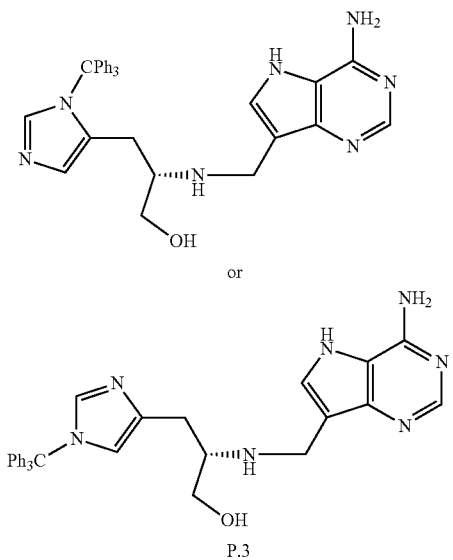

P.3 or (4S)-4-{[1-(Triphenylmethyl)-1H-imidazol-4-yl]methyl}-1,3-oxazolidin-2-one or (4S)-4-{[1-(triphenylmethyl)-1H-imidazol-5-yl]methyl}-1,3-oxazolidin-2-one (P.1). A modified literature procedure [Madrigal, et al.[14]] was followed. (S)-Histidinol dihydrochloride (0.500 g, 2.34 mmol) and diethyl carbonate (2.86 mL, 23.61 mmol) were stirred together in ethanol (24 mL), then sodium methoxide in methanol solution (25%, 1.6 mL, 7.0 mmol) added. The mixture was heated under reflux for 72 h then the solvent was evaporated and the residue chromatographed on silica gel (CHCl₃-MeOH-28% aq. NH₄OH, 9:1:0.1) to give (4S)-4-(1H-imidazol-4-ylmethyl)-1,3-oxazolidin-2-one as a colourless solid (0.26 g, 1.56 mmol, 90-95% pure). $^1$H NMR (500 MHz, CD₃OD): δ 7.61 (d, J=1.0 Hz, 1H), 6.93 (s, 1H), 4.45-4.40 (m, 1H), 4.18-4.12 (m, 2H), 2.86 (dd, J=14.7, 4.8 Hz, 1H), 2.80 (dd, J=14.8, 6.1 Hz, 1H). It was dissolved in DMF (4 mL) then triethylamine (0.42 mL, 3.00 mmol) and trityl chloride (0.489 g, 1.70 mmol) were added. The mixture was stirred for 60 h at rt then diluted with Et₂O (60 mL) and the mixture washed with H₂O (4×5 mL), brine (5 mL), dried and the solvent evaporated. The residue was chromatographed on silica gel (gradient of 0-5% MeOH in EtOAc) to give P.1 as a colourless foam (0.520 g, 54%). $^1$H NMR (500 MHz, CD₃OD): δ 7.41 (d, J=1.4 Hz, 1H), 7.39-7.34 (m, 9H), 7.16-7.11 (m, 6H), 6.82 (m, 1H), 4.39 (t, J=8.4 Hz, 1H), 4.19-4.11 (m, 2H), 2.78 (dd, J=14.6, 4.9 Hz, 1H), 2.73 (dd, J=14.6, 6.1 Hz, 1H). $^{13}$C NMR (125.7 MHz, CD₃OD, centre line δ 49.0): δ 162.1 (C), 143.6 (C×3), 139.8 (CH), 136.6 (C), 130.9 (CH), 129.32 (CH), 129.27 (CH), 121.6 (CH), 76.9 (C), 70.4 (CH₂), 53.4 (CH), 33.9 (CH₂). ESI-HRMS calcd for $C_{26}H_{23}N_3NaO_2^+$, (M+Na)⁺, 432.1683. found 432.1677.

(2S)-2-Amino-3-[1-(triphenylmethyl)-1H-imidazol-4-yl]propan-1-ol or (2S)-2-amino-3-[1-(triphenylmethyl)-1H-imidazol-5-yl]propan-1-ol (P.2). Compound P.1 (0.510 g, 1.25 mmol) was dissolved in 2-propanol (7 mL) and potassium hydroxide (2 M, 3 mL, 6 mmol) added. The mixture was heated at 80° C. for 6 h then silica gel was added to absorb all the solvent then the solvent was evaporated and the residue chromatographed on silica gel (CHCl₃-MeOH-28% aq. NH₄OH, 9:1:0.1) to give P.2 as a colourless gum (0.478 g, 100%). $^1$H NMR (500 MHz, CD₃OD): δ 7.40 (d, J=1.4 Hz, 1H), 7.38-7.34 (m, 9H), 7.18-7.13 (m, 6H), 6.75 (m, 1H), 3.52 (dd, J=10.9, 4.5 Hz, 1H), 3.35 (dd, J=10.9, 6.8 Hz, 1H), 3.09-3.03 (m, 1H), 2.65 (dd, J=14.4, 6.0 Hz, 1H), 2.50 (dd, J=14.4, 7.4 Hz, 1H). $^{13}$C NMR (125.7 MHz, CD₃OD, centre line δ 49.0): δ 143.7 (C), 139.7 (CH), 139.2 (C), 130.8 (CH), 129.3 (CH), 129.2 (CH), 121.0 (CH), 76.8 (C), 66.7 (CH₂), 53.8 (CH), 33.0 (CH₂). ESI-HRMS calcd for $C_{25}H_{26}N_3O^+$, (M+H)⁺, 384.2071. found 384.2068.

(2S)-2-[({4-Amino-5H-pyrrolo[3,2-d]pyrimidin-7-yl}methyl)amino]-3-[1-(triphenylmethyl)-1H-imidazol-4-yl]propan-1-ol or (2S)-2-[({4-amino-5H-pyrrolo[3,2-d]pyrimidin-7-yl}methyl)amino]-3-[1-(triphenylmethyl)-1H-imidazol-5-yl]propan-1-ol (P.3). Compound P.2 (0.200 g, 0.52 mmol), 9-deazaadenine (0.070 g, 0.52 mmol) and aq. formaldehyde solution (37%, 0.051 mL, 0.68 mmol) were heated at 70° C. in tert-butanol (3 mL) for 16 h. Silica gel was added to absorb all the solvent then the solvent was evaporated and the residue chromatographed on silica gel (10% 7M NH3/MeOH—CHCl₃) to give P.3 as a colourless foam (0.101 g, 37%). $^1$H NMR (500 MHz, CD₃OD): δ 8.03 (s, 1H), 7.39 (s, 1H), 7.35 (d, J=1.3 Hz, 1H), 7.33-7.29 (m, 9H), 7.12-7.08 (m, 6H), 6.75 (d, J=1.2 Hz, 1H), 3.96 (d, J=13.7 Hz, 1H), 3.93 (d, J=13.6 Hz, 1H), 3.61 (dd, J=11.3, 4.8 Hz, 1H), 3.49 (dd, J=11.3, 6.1 Hz, 1H), 3.02-2.97 (m, 1H), 2.72 (dd, J=14.5, 6.5 Hz, 1H), 2.69 (dd, J=14.5, 6.7 Hz, 1H). $^{13}$C NMR (125.7 MHz, CD₃OD, centre line δ 49.0): δ 152.0 (C), 150.8 (CH), 146.6 (C), 143.7 (C×3), 139.5 (CH), 139.2 (C), 130.8 (CH), 129.24 (CH), 129.20 (CH), 128.9 (CH), 121.2 (CH), 115.4 (C), 114.8 (C), 76.8 (C), 64.3 (CH₂), 59.4 (CH), 41.3 (CH₂), 30.7 (CH₂). ESI-HRMS calcd for $C_{32}H_{32}N_7O^+$, (M+H)⁺, 530.2663. found 530.2666.

(2S)-2-[({4-Amino-5H-pyrrolo[3,2-d]pyrimidin-7-yl}methyl)amino]-3-(1H-imidazol-4-yl)propan-1-ol (P.4). Trifluoroacetic acid (0.6 mL, 8 mmol) was added to a stirred solution of P.3 (0.100 g, 0.19 mmol) and triethylsilane (0.090 mL, 0.57 mmol) in CH₂Cl₂ (3 mL). After 2 h, the solvent was evaporated and the residue dissolved in MeOH and the solvent evaporated (3×). The residue was again dissolved in MeOH, silica gel added and the solvent evaporated. Flash chromatography on silica gel (CHCl₃-MeOH-28% aq. NH₄OH, 7:2.5:0.5) gave P.4 as a colourless gum which crystallized on standing (0.050 g, 92%). $^1$H NMR (500 MHz, CD$_3$OD): δ 8.14 (s, 1H), 7.52 (d, J=0.9 Hz, 1H), 7.42 (s, 1H), 6.80 (s, 1H), 4.01 (d, J=13.6 Hz, 1H), 3.98 (d, J=13.6 Hz, 1H), 3.63 (dd, J=11.3, 4.7 Hz, 1H), 3.50 (dd, J=11.3, 5.9 Hz, 1H), 3.01-2.96 (m, 1H), 2.76 (d, J=6.7 Hz, 2H). $^{13}$C NMR (125.7 MHz, CD$_3$OD, centre line δ 49.0): δ 152.0 (C), 150.8 (CH), 146.6 (C), 136.1 (CH), 134.8 (b, C), 129.0 (CH), 119.4 (b, CH), 115.4 (C), 114.3 (C), 64.0 (CH$_2$), 59.3 (CH), 41.3 (CH$_2$), 29.2 (CH$_2$). ESI-HRMS calcd for C$_{13}$H$_{18}$N$_7$O$^+$, (M+H)$^+$, 288.1568. found 288.1567.

Example Q

Synthesis of (2R)-2-[({4-amino-5H-pyrrolo[3,2-d]pyrimidin-7-yl}methyl)amino]-3-(butylsulfanyl)propan-1-ol (Q.2)

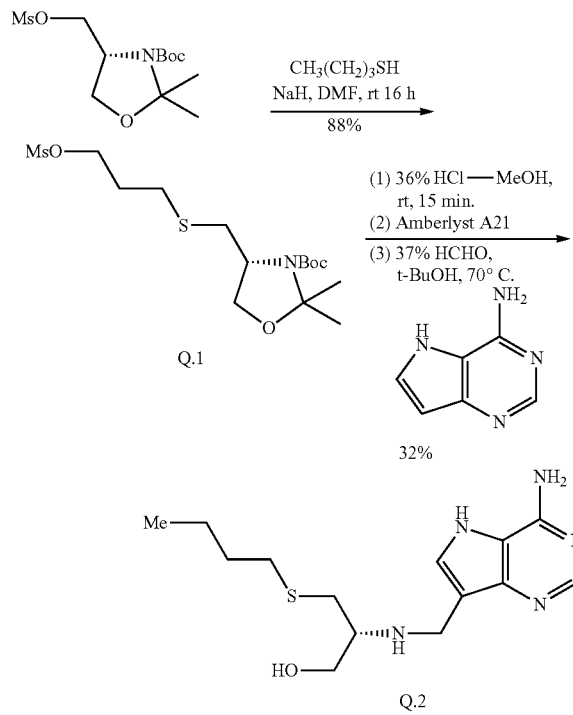

tert-Butyl (4R)-4-[(butylsulfanyl)methyl]-2,2-dimethyl-1,3-oxazolidine-3-carboxylate (Q.1). Sodium hydride (60%, 0.097 g, 2.4 mmol) was added in portions to a solution of butane-1-thiol (0.53 mL, 4.85 mmol) in DMF (5 mL). After 15 min a solution of the crude mesylate (0.500 g, 1.62 mmol, from step 1 of the preparation of K.1) in DMF (1 mL) was added. The mixture was stirred for 16 h then H$_2$O (6 mL) added. After extraction with Et$_2$O (100 mL), the extract was washed with H$_2$O (4×5 mL), brine (5 mL), dried and the solvent evaporated. The residue was chromatographed on silica gel (gradient of 0-10% EtOAc in hexanes) to give Q.1 as a colourless oil (0.429 g, 88%). $^1$H NMR (500 MHz, CDCl$_3$): δ 4.06-3.92 (m, 2.5H), 3.91-3.85 (m, 0.5H), 2.94 (d, J=13.0 Hz, 0.5H), 2.80 (d, J=13.0 Hz, 0.5H), 2.62-2.47 (m, 3H), 1.65-1.53 (m, 5H), 1.50-1.35 (m, 14H), 0.91 (t, J=7.1 Hz, 3H). $^{13}$C NMR (125.7 MHz, CDCl$_3$, centre line δ 77.0): δ 152.1, 151.4 (C), 94.3, 93.7 (C), 80.2, 79.9 (C), 66.5, 66.3 (CH$_2$), 57.4, 57.2 (CH), 34.6, 33.9 (CH$_2$), 32.0, 31.9 (2×CH$_2$), 28.5, 28.4 (CH$_3$), 27.7, 26.9 (CH$_3$), 24.5, 23.2 (CH$_3$), 21.9 (CH$_2$), 13.6 (CH$_3$). ESI-HRMS calcd for C$_{15}$H$_{29}$NNaO$_3$S$^+$, (M+Na)$^+$, 326.1761. found 326.1760.

(2R)-2-[({4-Amino-5H-pyrrolo[3,2-d]pyrimidin-7-yl}methyl)amino]-3-(butylsulfanyl)propan-1-ol (Q.2). Compound Q.1 (0.400 g, 1.32 mmol) was dissolved in MeOH (4 mL) and aq. hydrochloric acid (36%, 1 mL) was added. After 15 min the solvent was evaporated and the resulting gum dissolved in MeOH (10 mL) and neutralized with Amberlyst A21 resin then passed through a short column of the same resin and eluted with MeOH. The fractions containing product were evaporated to an oily residue that was dissolved in tert butanol (4 mL) then 9-deazaadenine (0.177 g, 1.32 mmol) and aq. formaldehyde solution (37%, 0.12 mL, 1.60 mmol) added and the mixture stirred at 70° C. for 16 h. Silica gel was added to absorb all the solvent then the solvent was evaporated and the residue chromatographed on silica gel (gradient of 5-15% 7M NH$_3$/MeOH in CHCl$_3$) to give Q.2 as a colourless solid (0.131 g, 32%). $^1$H NMR (500 MHz, CD$_3$OD): δ 8.16 (s, 1H), 7.49 (s, 1H), 4.06 (d, J=13.8 Hz, 1H), 3.97 (d, J=13.9 Hz, 1H), 3.69 (dd, J=11.2, 5.1 Hz, 1H), 3.63 (dd, J=11.2, 5.4 Hz, 1H), 2.81-2.76 (m, 1H), 2.69 (dd, J=13.5, 6.3 Hz, 1H), 2.53 (dd, J=13.5, 6.9 Hz, 1H), 2.31 (ddd, J=12.5, 8.0, 6.5 Hz, 1H), 2.25 (ddd, J=12.5, 8.1, 6.7 Hz, 1H), 1.45-1.35 (m, 2H), 1.33-1.25 (m, 2H), 0.85 (t, J=7.3 Hz, 3H). $^{13}$C NMR (125.7 MHz, CD$_3$OD, centre line δ 49.0): δ 152.1 (C), 150.9 (CH), 146.6 (C), 129.1 (CH), 115.5 (C), 114.6 (C), 63.9 (CH$_2$), 57.8 (CH), 41.2 (CH$_2$), 34.5 (CH$_2$), 32.7 (CH$_2$), 32.6 (CH$_2$), 22.9 (CH$_2$), 13.9 (CH$_3$). ESI-HRMS calcd for C$_{14}$H$_{24}$N$_5$OS$^+$, (M+H)$^+$, 310.1697. found 310.1702.

Example R

Synthesis of (2R)-2-[({4-amino-5H-pyrrolo[3,2-d]pyrimidin-7-yl}methyl)amino]-3-(heptylsulfanyl)propan-1-ol (R.2)

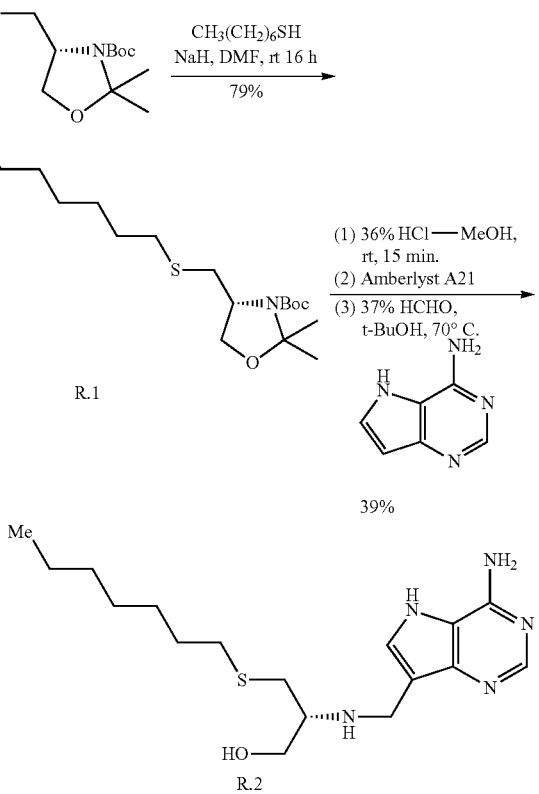

tert-Butyl (4R)-4-[(heptylsulfanyl)methyl]-2,2-dimethyl-1,3-oxazolidine-3-carboxylate (R.1). Sodium hydride (60%, 0.162 g, 4.05 mmol) was added in portions to a solution of heptane-1-thiol (0.641 g, 4.85 mmol) in DMF (5 mL) at rt. After 15 min, a solution of the crude mesylate (0.500 g, 1.62 mmol, from step 1 of the preparation of K.1) in DMF (1 mL) was added. The mixture was stirred for 16 h then H$_2$O (6 mL) added. After extraction with Et$_2$O (100 mL), the extract was washed with H$_2$O (4×5 mL), brine (5 mL) dried and evaporated to an oily residue that was chromatographed on silica gel (gradient of 0-12% EtOAc in hexanes) to give R.1 as a colourless oil (0.443 g, 79%). $^1$H NMR (500 MHz, CDCl$_3$): δ 4.05-3.98 (m, 1.5H), 3.97-3.93 (m, 1H), 3.91-3.85 (m, 0.5H), 2.93 (d, J=13.5 Hz, 0.5H), 2.80 (d, J=12.9 Hz, 0.5H), 2.62-2.45 (m, 3H), 1.63-1.53 (m, 5H), 1.51-1.43 (m, 12H), 1.41-1.22 (m, 8H), 0.88 (t, J=6.8 Hz, 3H). $^{13}$C NMR (125.7 MHz, CDCl$_3$, centre line δ 77.0): δ 152.1, 151.5 (C), 94.3, 93.7 (C), 80.2, 79.9 (C), 66.5, 66.3 (CH$_2$), 57.4, 57.2 (CH), 34.7, 33.8 (CH$_2$), 32.4, 31.7 (2×CH$_2$), 30.0, 29.8 (CH$_2$), 28.9, 28.8, (2×CH$_2$), 28.5, 28.4 (CH$_3$), 27.7, 26.9 (CH$_3$), 24.5, 23.2 (CH$_3$), 22.6 (CH$_2$), 14.0 (CH$_3$). ESI-HRMS calcd for C$_{18}$H$_{35}$NNaO$_3$S$^+$, (M+Na)$^+$, 368.2230. found 368.2227.

(2R)-2-[({4-Amino-5H-pyrrolo[3,2-d]pyrimidin-7-yl}methyl)amino]-3-(heptylsulfanyl)propan-1-ol (R.2). Compound R.1 (0.420 g, 1.22 mmol) was dissolved in MeOH (4 mL) and aq. hydrochloric acid (36%, 1 mL) added. After 15 min the solvent was evaporated to a gum that was dissolved in a 7:3 mixture of MeOH—CHCl$_3$ (10 mL) and neutralized with Amberlyst A21 resin then passed through a short column of the same resin and eluted with a 7:3 mixture of MeOH—CHCl$_3$. The fractions containing product were evaporated to an oily residue that was dissolved in tert-butanol (4 mL) then 9-deazaadenine (0.130 g, 0.97 mmol) and aq. formaldehyde solution (37%, 0.087 mL, 1.16 mmol) were added and the mixture stirred at 70° C. for 16 h. Silica gel was added to absorb all the solvent then the solvent was evaporated and the residue chromatographed on silica gel (gradient of 5-15% 7M NH$_3$/MeOH in CHCl$_3$) to give crude R.2 (210 mg). Further chromatography on silica gel (gradient of 0-5% aq. NH$_4$OH (28%) in 2-PrOH) gave R.2 as a colourless solid (0.134 g, 34%). $^1$H NMR (500 MHz, CD$_3$OD): δ 8.16 (s, 1H), 7.49 (s, 1H), 4.06 (d, J=13.8 Hz, 1H), 3.97 (d, J=13.8 Hz, 1H), 3.69 (dd, J=11.2, 5.1 Hz, 1H), 3.63 (dd, J=11.2, 5.4 Hz, 1H), 2.81-2.76 (m, 1H), 2.69 (dd, J=13.5, 6.3 Hz, 1H), 2.54 (dd, J=13.5, 6.9 Hz, 1H), 2.32 (ddd, J=12.5, 7.9, 6.8 Hz, 1H), 2.26 (ddd, J=12.6, 7.9, 6.9 Hz, 1H), 1.47-1.37 (m, 2H), 1.33-1.20 (m, 8H), 0.88 (t, J=7.1 Hz, 3H). $^{13}$C NMR (125.7 MHz, CD$_3$OD, centre line δ 49.0): δ 152.1 (C), 150.9 (CH), 146.6 (C), 129.1 (CH), 115.4 (C), 114.6 (C), 63.8 (CH$_2$), 57.9 (CH), 41.2 (CH$_2$), 34.5 (CH$_2$), 32.9 (CH$_2$×2), 30.6 (CH$_2$), 30.0 (CH$_2$), 29.8 (CH$_2$), 26.6 (CH$_2$), 14.4 (CH$_3$). ESI-HRMS calcd for C$_{17}$H$_{30}$N$_5$OS$^+$, (M+H)$^+$, 352.2166. found 352.2157.

Example S

Synthesis of (2S)-2-[({4-amino-5H-pyrrolo[3,2-d]pyrimidin-7-yl}methyl)amino]heptan-1-ol (S.2)

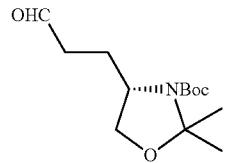

(1) PH$_3$P$^+$CH$_2$CH$_3$Br$^-$
KO$^t$Bu, CH$_2$Cl$_2$
0° C., 20 min
(2) H$_2$, Pd—C,
EtOAc, rt 16 h
45%

-continued

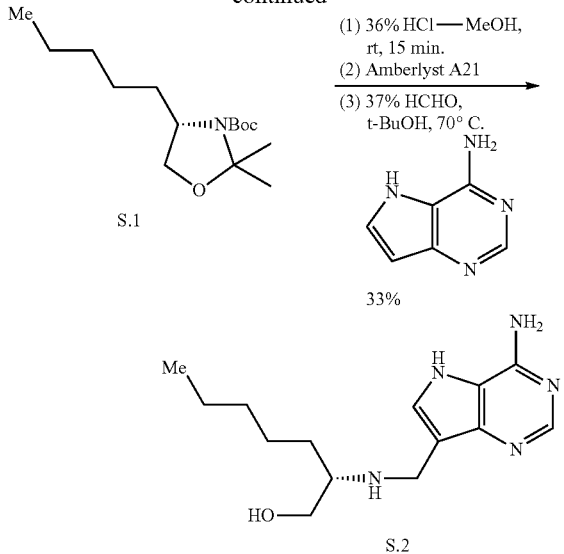

(1) 36% HCl—MeOH,
rt, 15 min.
(2) Amberlyst A21
(3) 37% HCHO,
t-BuOH, 70° C.

33% tert-Butyl (4S)-2,2-dimethyl-4-pentyl-1,3-oxazolidine-3-carboxylate (S.1). tert-Butyl (4S)-2,2-dimethyl-4-(3-oxopropyl)-1,3-oxazolidine-3-carboxylate [Goswami, et al.$^{15}$] (0.400 g, 1.55 mmol, purified on silica gel with a gradient of 0-50% EtOAc in hexanes) and ethyltriphenylphosphonium bromide [Paleček, J. et al.$^{16}$] (0.866 g, 2.33 mmol, dried over P$_2$O$_5$ then evaporated 2× from dry toluene) were dissolved in anhydrous CH$_2$Cl$_2$ (7 mL) and cooled at 0° C. A solution of potassium tert-butoxide in THF (1.6 M, 1.5 mL, 2.4 mmol) was added dropwise and the mixture stirred for 20 min. [method similar to that described in Ksander, et al.$^{17}$] Silica gel was added to absorb all the solvent then the solvent was evaporated and the residue chromatographed on silica gel (gradient of 0-5% EtOAc in hexanes to give the Wittig product as a colourless oil (0.304 g, 73%). The latter product (0.430 g, 1.60 mmol) and 10% Pd on carbon (60 mg) were stirred together in EtOAc (15 mL) under a hydrogen atmosphere for 16 h. The mixture was filtered through Celite then the filtrate evaporated and the residue chromatographed on silica gel (gradient of 0-5% EtOAc in hexanes) to give S.1 as a colourless oil (0.359 g, 61%). $^1$H NMR (500 MHz, CDCl$_3$): δ 3.93-3.71 (m, 3H), 1.83-1.42 (m, 17H), 1.36-1.20 (m, 6H), 0.93-0.80 (m, 3H). $^{13}$C NMR (125.7 MHz, CDCl$_3$, centre line δ 77.0): δ 152.1, 151.9 (C), 93.6, 93.0 (C), 79.8, 79.3 (C), 67.1, 66.8 (CH$_2$), 57.8, 57.4 (CH), 33.6, 32.8 (CH$_2$), 31.7 (CH$_2$), 28.5 (CH$_3$), 27.5, 26.7 (CH$_3$), 25.9 (CH$_2$), 24.6, 23.3 (CH$_3$), 22.6 (CH$_2$), 13.9 (CH$_3$). ESI-HRMS calcd for C$_{15}$H$_{29}$NNaO$_3^+$, (M+Na)$^+$, 294.2040. found 294.2038.

(2S)-2-[({4-Amino-5H-pyrrolo[3,2-d]pyrimidin-7-yl}methyl)amino]heptan-1-ol (S.2). Compound S.1 (0.358 g, 1.32 mmol) was dissolved in MeOH (4 mL) and aq. hydrochloric acid (36%, 1 mL) added. After 15 min the solvent was evaporated to a colourless solid that was dissolved in MeOH (10 mL), neutralized with Amberlyst A21 resin then passed through a short column of the same resin and eluted with MeOH. The fractions containing product were evaporated to an oily residue that was dissolved in tert-butanol (4 mL) then 9-deazaadenine (0.177 g, 1.32 mmol) and aq. formaldehyde solution (0.12 mL, 1.59 mmol) were added and the mixture stirred at 70° C. for 16 h. Silica gel was added to absorb all the solvent then the solvent was evaporated and the residue chromatographed on silica gel (gradient of 5-15% 7M NH$_3$/MeOH in CHCl$_3$) to give S.2 as a colourless solid (0.122 g, 33%). $^1$H NMR (500 MHz, CD$_3$OD): δ 8.16 (s, 1H), 7.47 (s, 1H), 3.64 (dd, J=11.2, 4.5 Hz, 1H), 3.48 (dd, J=11.2, 6.5 Hz, 1H), 2.68-2.64 (m, 1H), 1.52-1.38 (m, 2H), 1.32-1.17 (m, 6H), 0.86 (t, J=7.1 Hz, 3H). $^{13}$C NMR (125.7 MHz, CD$_3$OD, centre line δ 49.0): δ 152.1 (C), 150.8 (CH), 146.6 (C), 129.0 (CH), 115.4 (C), 114.8 (C), 64.4 (CH$_2$), 59.2 (CH), 41.2 (CH$_2$), 33.1 (CH$_2$), 32.0 (CH$_2$), 26.8 (CH$_2$), 23.6 (CH$_2$), 14.4 (CH$_3$). ESI-HRMS calcd for C$_{14}$H$_{24}$N$_5$O$^+$, (M+H)$^+$, 278.1976. found 278.1974.

Example T

Synthesis of (2S)-2-[({4-amino-5H-pyrrolo[3,2-d]pyrimidin-7-yl}methyl)amino]octan-1-ol (T.2)

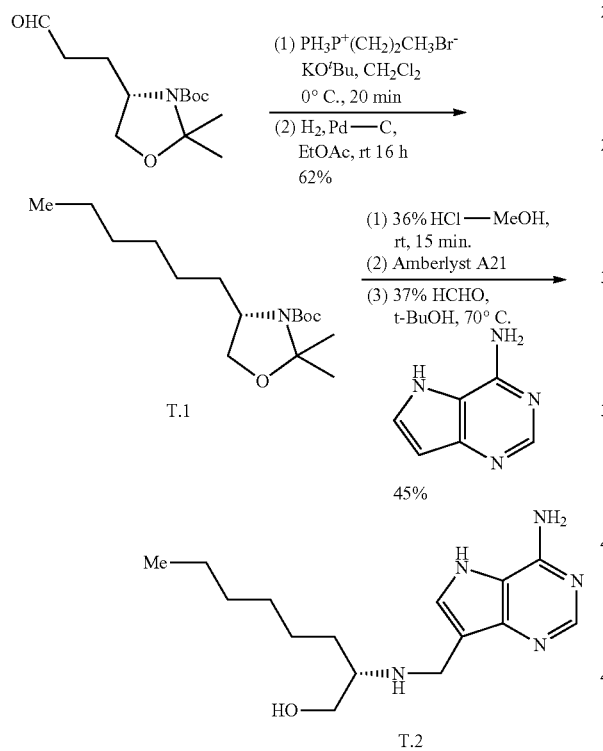

tert-Butyl (4S)-4-hexyl-2,2-dimethyl-1,3-oxazolidine-3-carboxylate (T.1)

tert-Butyl (4S)-2,2-dimethyl-4-(3-oxopropyl)-1,3-oxazolidine-3-carboxylate [Goswami, et al.[15]] (0.500 g, 1.94 mmol, purified on silica gel with a gradient of 0-50% EtOAc in hexanes) and n-propyltriphenylphosphonium bromide (1.12 g, 2.91 mmol, dried over P$_2$O$_5$ then evaporated 2× from dry toluene) were dissolved in anhydrous CH$_2$Cl$_2$ (7 mL) and cooled to 0° C. A solution of potassium tert-butoxide in THF (1.6 M, 1.8 mL, 2.90 mmol) was added dropwise and the mixture stirred for 20 min. [method similar to that described in Ksander, et al.[17]] Silica gel was added to absorb all the solvent then the solvent was evaporated and the residue chromatographed on silica gel (gradient of 0-4% EtOAc in hexanes to give the Wittig product as a colourless oil (0.361 g, 66%). The latter product (0.360 g, 1.27 mmol) and 10% Pd on carbon (60 mg) were stirred together in EtOAc (15 mL) under a hydrogen atmosphere for 16 h. The mixture was filtered through Celite then the filtrate evaporated and the residue chromatographed on silica gel (gradient of 0-5% EtOAc in hexanes) to give T.1 as a colourless oil (0.342 g, 94%). $^1$H NMR (500 MHz, CDCl$_3$): δ 3.93-3.71 (m, 3H), 1.82-1.42 (m, 17H), 1.36-1.19 (m, 8H), 0.92-0.85 (m, 3H). $^{13}$C NMR (125.7 MHz, CDCl$_3$, centre line δ 77.0): δ 152.1, 151.9 (C), 93.5, 93.0 (C), 79.8, 79.3 (C), 67.1, 66.7 (CH$_2$), 57.8, 57.4 (CH), 33.6, 32.9 (CH$_2$), 31.8 (CH$_2$), 29.1 (CH$_2$), 28.5 (CH$_3$), 27.5, 26.7 (CH$_3$), 26.2 (CH$_2$), 24.6, 23.3 (CH$_3$), 22.5 (CH$_2$), 14.0 (CH$_3$). ESI-HRMS calcd for C$_{16}$H$_{32}$NO$_{3+}$, (M+H)$^+$, 286.2377. found 286.2375.

(2S)-2-[({4-Amino-5H-pyrrolo[3,2-d]pyrimidin-7-yl}methyl)amino]octan-1-ol (T.2). Compound T.1 (0.320 g, 1.12 mmol) was dissolved in MeOH (4 mL) and aq. hydrochloric acid (36%, 1 mL) added. After 15 min the solvent was evaporated to a colourless solid that was dissolved in a 4:1 mixture MeOH—CHCl$_3$ (10 mL), neutralized with Amberlyst A21 resin then passed through a short column of the same resin and eluted with 4:1 MeOH—CHCl$_3$. The fractions containing product were evaporated to a yellow solid that was dissolved in tert-butanol (4 mL) then 9-deazaadenine (0.150 g, 1.12 mmol) and aq. formaldehyde solution (37%, 0.101 mL, 1.35 mmol) were added and the mixture was stirred at 70° C. for 16 h. Silica gel was added to absorb all the solvent then the solvent was evaporated and the residue chromatographed on silica gel (gradient of 5-15% 7M NH$_3$/MeOH in CHCl$_3$) to give T.2 as a colourless solid (0.148 g, 45%). $^1$H NMR (500 MHz, 1:1 CD$_3$OD-CDCl$_3$): δ 8.20 (s, 1H), 7.40 (s, 1H), 3.98 (d, J=13.7 Hz, 1H), 3.95 (d, J=13.7 Hz, 1H), 3.73 (dd, J=11.4, 4.0 Hz, 1H), 3.50 (dd, J=11.4, 6.6 Hz, 1H), 2.74-2.69 (m, 1H), 1.54-1.39 (m, 2H), 1.34-1.22 (m, 8H), 0.88 (t, J=6.9 Hz, 3H). $^{13}$C NMR (125.7 MHz, 1:1 CD$_3$OD-CDCl$_3$, centre lines δ 49.0 and δ 78.3): δ 151.2 (C), 150.2 (CH), 146.0 (C), 128.1 (CH), 115.0 (C), 114.2 (C), 63.6 (CH$_2$), 59.0 (CH), 40.7 (CH$_2$), 32.4 (CH$_2$), 31.6 (CH$_2$), 30.0 (CH$_2$), 26.7 (CH$_2$), 23.1 (CH$_2$), 14.3 (CH$_3$). ESI-HRMS calcd for C$_{15}$H$_{25}$N$_5$NaO$^+$, (M+Na)$^+$, 314.1952. found 314.1953.

Example U

Synthesis of (2S)-2-[({4-amino-5H-pyrrolo[3,2-d]pyrimidin-7-yl}methyl)amino]undecan-1-ol (U.2)

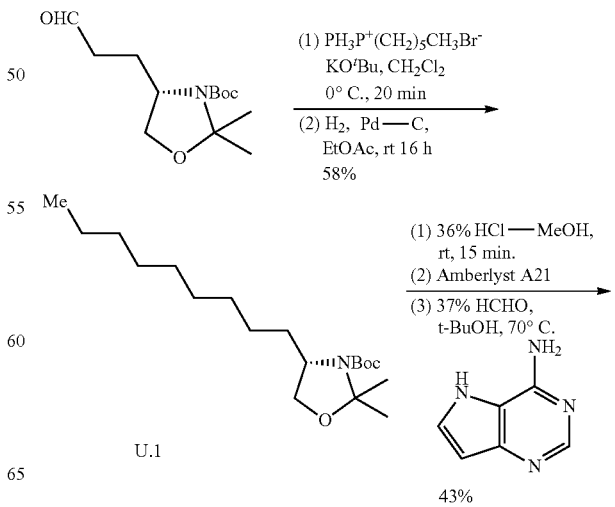

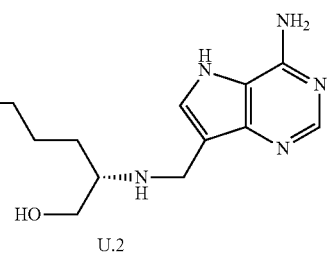

tert-Butyl (4S)-2, 2-dimethyl-4-nonyl-1, 3-oxazolidine-3-carboxylate (U.1). Step 1. Triphenylphosphine (3.70 g, 14.11 mmol) and 1-bromohexane (2.97 mL, 21.16 mmol) were stirred and heated under reflux in toluene (10 mL) for 16 h. The resulting n-hexyltriphenylphosphonium bromide (3.30 g, 55%) was filtered off and dried over $P_2O_5$ then evaporated 2× from dry toluene.

Step 2. The phosphonium salt from step 1 (1.30 g, 3.04 mmol) and tert-butyl (4S)-2,2-dimethyl-4-(3-oxopropyl)-1,3-oxazolidine-3-carboxylate [Goswami, et al.[15]] (0.500 g, 1.94 mmol, purified on silica gel with a gradient of 0-50% EtOAc in hexanes) were dissolved in $CH_2Cl_2$ (7 mL) and cooled at 0° C. A solution of potassium tert-butoxide in THF (1.6 M, 1.9 mL, 3.00 mmol) was added dropwise and the mixture stirred for 20 min. [method similar to that described in Ksander, et al.[17]]. Silica gel was added to absorb all the solvent then the solvent was evaporated and the residue chromatographed on silica gel (gradient of 0-5% EtOAc in hexanes to give the Wittig product as a colourless oil (0.370 g, 59%). The latter product (0.340 g, 1.04 mmol) and 10% Pd on carbon (60 mg) were stirred together in EtOAc (15 mL) under a hydrogen atmosphere for 16 h. The mixture was filtered through Celite and the filtrate evaporated and the residue chromatographed on silica gel (gradient of 0-5% EtOAc in hexanes) to give U.1 as a colourless oil (0.340 g, 99%). $^1$H NMR (500 MHz, $CDCl_3$): δ 3.93-3.70 (m, 3H), 1.82-1.42 (m, 17H), 1.35-1.82 (m, 14H), 0.88 (t, J=6.9 Hz, 3H). $^{13}$C NMR (125.7 MHz, $CDCl_3$, centre line δ 77.0): δ 152.2, 151.9 (C), 93.6, 93.0 (C), 79.8, 79.3 (C), 67.1, 66.8 ($CH_2$), 57.8, 57.5 (CH), 33.6, 32.9 ($CH_2$), 31.9 ($CH_2$), 29.6, 29.5, 29.3 (4×$CH_2$), 28.5 ($CH_3$), 27.5, 26.8 ($CH_3$), 26.3 ($CH_2$), 24.6, 23.3 ($CH_3$), 22.6 ($CH_2$), 14.1 ($CH_3$). ESI-HRMS calcd for $C_{19}H_{37}NNaO_3^+$, (M+Na)$^+$, 350.2666. found 350.2663.

(2S)-2-[({4-Amino-5H-pyrrolo[3,2-d]pyrimidin-7-yl}methyl)amino]undecan-1-ol (U.2). Compound U.1 (0.310 g, 0.947 mmol) was dissolved in MeOH (4 mL) and aq. hydrochloric acid (36%, 1 mL) added. After 15 min the solvent was evaporated to a colourless solid that was dissolved in a 4:1 mixture MeOH—$CHCl_3$, neutralized with Amberlyst A21 resin then passed through a short column of the same resin and eluted with 4:1 MeOH—$CHCl_3$. The fractions containing product were evaporated to a yellow oil that was dissolved in tert-butanol (4 mL) then 9-deazaadenine (0.127 g, 0.95 mmol) and aq. formaldehyde solution (37%, 0.085 mL, 1.10 mmol) were added and the mixture was stirred at 70° C. for 16 h. Silica gel was added to absorb all the solvent then the solvent was evaporated and the residue chromatographed on silica gel (gradient of 5-15% 7M $NH_3$/MeOH in $CHCl_3$) to give U.2 as a colourless solid (0.135 g, 43%). $^1$H NMR (500 MHz, 1:1 $CD_3OD$-$CDCl_3$): δ 8.20 (s, 1H), 7.40 (s, 1H), 3.96 (s, 1H), 3.73 (dd, J=11.4, 3.9 Hz, 1H), 3.50 (dd, J=11.4, 6.6 Hz, 1H), 2.74-2.69 (m, 1H), 1.55-1.39 (m, 2H), 1.35-1.21 (m, 14H), 0.89 (t, J=7.0 Hz, 3H). $^{13}$C NMR (125.7 MHz, 1:1 $CD_3OD$-$CDCl_3$, centre lines δ 49.0 and δ 78.3): δ 151.2 (C), 150.2 (CH), 146.0 (C), 128.1 (CH), 115.0 (C), 114.2 (C), 63.6 ($CH_2$), 59.0 (CH), 40.7 ($CH_2$), 32.5 ($CH_2$), 31.6 ($CH_2$), 30.4 ($CH_2$), 30.1 (2×$CH_2$), 29.9 ($CH_2$), 26.8 ($CH_2$), 23.2 ($CH_2$), 14.3 ($CH_3$). ESI-HRMS calcd for $C_{18}H_{32}N_5O^+$, (M+H)$^+$, 334.2602. found 334.2605.

Example V

Synthesis of (2R)-2-[({4-amino-5H-pyrrolo[3,2-d]pyrimidin-7-yl}methyl)amino]-3-(pyrazin-2-ylsulfanyl)propan-1-ol (V.2)

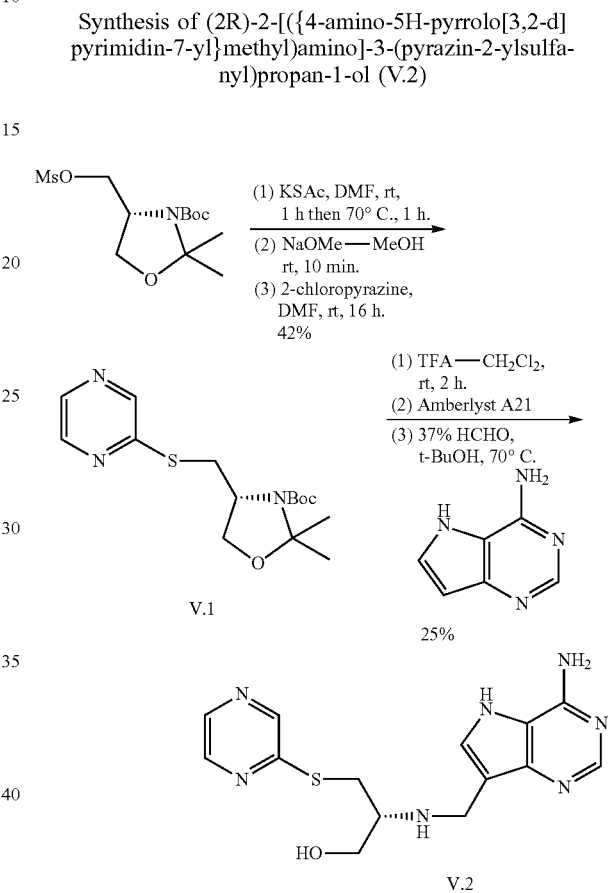

tert-Butyl (4R)-2,2-dimethyl-4-[(pyrazin-2-ylsulfanyl)methyl]-1,3-oxazolidine-3-carboxylate (V.1). Step 1. Potassium thioacetate (0.588 g, 5.05 mmol)) and mesylate from step 1 of the preparation of K.1 (0.520 g, 1.68 mmol) were stirred together in DMF (5 mL) at rt for 16 h then at 70° C. for 1 h. Water (5 mL) was added and the mixture extracted with $Et_2O$ (100 mL). The extract was washed with $H_2O$ (4×5 mL), brine (5 mL), dried, the solvent evaporated and the residue chromatographed on silica gel (gradient of 0-30% EtOAc in hexanes) to give tert-butyl (4R)-4-[(acetylsulfanyl)methyl]-2,2-dimethyl-1,3-oxazolidine-3-carboxylate as a colourless oil (0.347 g, 71%)

Step 2. Sodium methoxide in methanol solution (25%, 0.27 mL, 1.2 mmol) was added to a solution of the thioacetate from step 1 (0.340 g, 1.17 mmol) in MeOH (5 mL)). After 10 mins the solvent was evaporated and the residue dissolved in DMF (5 mL) then 2-chloropyrazine (0.32 mL, 3.6 mmol) added and the mixture stirred for 16 h. Water (5 mL) was added then the mixture was extracted with $Et_2O$ (100 mL). The extract was washed with $H_2O$ (4×5 mL), brine (5 mL), dried and evaporated. The residue was chromatographed on silica gel (gradient of 0-30% EtOAc in hexanes) to give V.1 as a colourless oil (0.224 g, 59%). $^1$H NMR (500 MHz, CDCl$_3$): δ 8.55, 8.48 (2× bs, 1H), 8.36, 8.33 (2× bs, 1H), 8.22 (bs, 1H), 4.23, 4.14 (2× bs, 1H), 4.06-3.93 (m, 2H), 3.76-3.63 (m, 1H), 3.37-3.27 (m, 0.5H), 3.17-3.07 (m, 0.5H), 1.67-1.59 (m, 3H), 1.53-1.45 (m, 12H). $^{13}$C NMR (125.7 MHz, CDCl$_3$, centre line δ 77.0): δ 156.5, 156.1 (C), 152.2, 151.6 (C), 143.7, 143.6 (2×CH), 139.8, 139.7 (CH), 94.5, 93.9 (C), 80.5, 80.2 (C), 66.4, 66.3 (CH$_2$), 56.9, 56.5 (CH), 31.4, 31.0 (CH$_2$), 28.5 (CH$_3$), 27.5, 26.9 (CH$_3$), 24.4, 23.2 (CH$_3$). ESI-HRMS calcd for C$_{15}$H$_{23}$N$_3$NaO$_3$S$^+$ (M+Na)$^+$, 348.1353. found 348.1350.

(2R)-2-[({4-Amino-5H-pyrrolo[3,2-d]pyrimidin-7-yl}methyl)amino]-3-(pyrazin-2-ylsulfanyl)propan-1-ol (V.2). Compound V.1 (0.220 g, 0.68 mmol) was dissolved in CH$_2$Cl$_2$ (8 mL) and trifluoroacetic acid (2 mL) added. After 2 h the solvent was evaporated and the residue dissolved in MeOH (10 mL) and neutralized with Amberlyst A21 resin then passed through a short column of the same resin and eluted with MeOH. The fractions containing product were evaporated to a yellow gum that was dissolved in tert-butanol (4 mL) then aq. formaldehyde solution (37%, 0.061 mL, 0.81 mmol) and 9-deazaadenine (0.091 g, 0.68 mmol) were added and the mixture heated at 70° C. for 16 h. Silica gel was added to absorb all the solvent then the solvent was evaporated and the residue chromatographed on silica gel (gradient of 10-15% 7M NH$_3$/MeOH in CHCl$_3$) to give V.2 as a colourless solid (0.055 g, 25%). $^1$H NMR (500 MHz, CD$_3$OD): δ 8.35 (d, J=1.5 Hz, 1H), 8.28 (dd, J=2.6, 1.7 Hz, 1H), 8.14 (d, J=2.7 Hz, 1H), 8.12 (s, 1H), 7.43 (s, 1H), 4.05 (d, J=13.9 Hz, 1H), 4.02 (d, J=13.8 Hz, 1H), 3.74 (dd, J=11.3, 4.9 Hz, 1H), 3.64 (dd, J=11.3, 5.5 Hz, 1H), 3.39-3.31 (m, 2H+residual deuterated solvent), 3.01-2.97 (m, 1H). $^{13}$C NMR (125.7 MHz, CD$_3$OD, centre line δ 49.0): δ 158.2 (C), 152.0 (C), 150.8 (CH), 146.5 (C), 145.2 (CH), 144.6 (CH), 140.3 (CH), 129.0 (CH), 115.4 (C), 114.7 (C), 63.7 (CH$_2$), 58.4 (CH), 41.4 (CH$_2$), 31.6 (CH$_2$). ESI-HRMS calcd C$_{14}$H$_{18}$N$_7$OS$^+$ (M+H)$^+$, 332.1289. found 332.1287.

Example W (2R)-2-[({4-Amino-5H-pyrrolo[3,2-d]pyrimidin-7-yl}methyl)amino]-3-(methylsulfanyl)propan-1-ol (W.1)

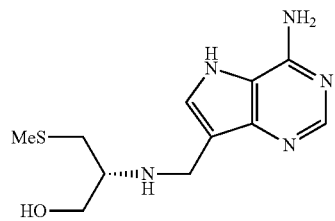

Prepared according to the literature [Clinch, et al.$^{18}$].

Example X (2S)-2-[({4-Amino-5H-pyrrolo[3, 2-d]pyrimidin-7-yl}methyl)amino]-3-(methylsulfanyl)propan-1-ol (X1)

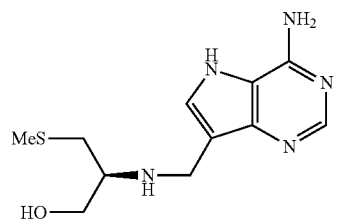

Prepared according to the literature [Clinch, et al.$^{18}$].

Example Y (2R,3S)-2-[({4-Amino-5H-pyrrolo[3, 2-d]pyrimidin-7-yl}methyl)amino]-4-(methylsulfanyl)butane-1,3-diol (Y.1)

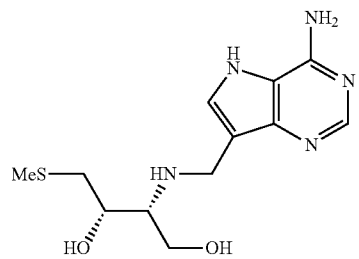

Prepared according to the literature [Clinch, et al.$^{18}$].

Example Z (2S,3R)-2-[({4-Amino-5H-pyrrolo[3, 2-d]pyrimidin-7-yl}methyl)amino]-4-(methylsulfanyl)butane-1,3-diol (Z.1)

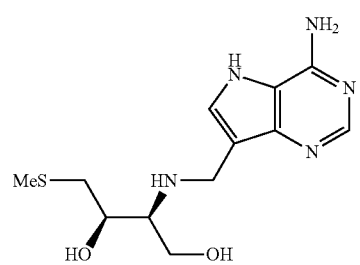

Prepared according to the literature [Clinch, et al.$^{18}$].

Example AA

Synthesis of 7-[(octylamino)methyl]-5H-pyrrolo[3,2-d]pyrimidin-4-amine (AA.1)

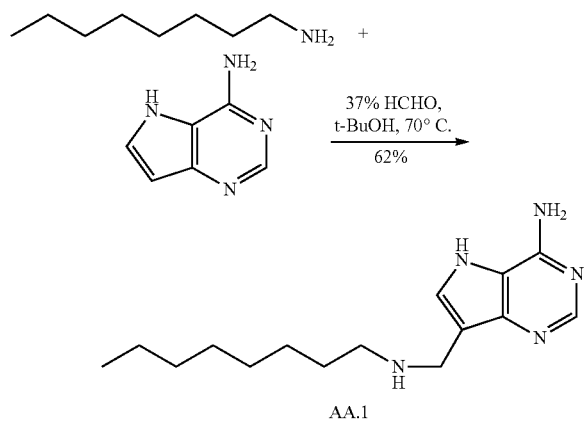

7-[(Octylamino)methyl]-5H-pyrrolo[3, 2-d]pyrimidin-4-amine (AA.1) Octan-1-amine (0.100 g, 0.77 mmol), aq. formaldehyde solution (37%, 0.076 mL, 1.01 mmol) and 9-deazaadenine (0.105 g, 0.78 mmol) were heated in tert-butanol (3 mL) at 70° C. for 16 h. Silica gel was added to absorb all the solvent then the solvent was evaporated and the residue chromatographed on silica gel (gradient of 5-15% 7 M $NH_3$/MeOH in $CHCl_3$) to give AA.1 as a colourless solid (0.132 g, 62%). $^1$H NMR (500 MHz, $CD_3OD$): δ 8.16 (s, 1H), 7.46 (s, 1H), 3.91 (s, 2H), 2.61 (t, J=7.5 Hz, 2H), 1.52 (pent, J=7.4 Hz, 2H), 1.34-1.21 (m, 10H), 0.88 (t, J=7.1 Hz, 3H). $^{13}$C NMR (125.7 MHz, $CD_3OD$ centre line δ 49.0): δ 152.1 (C), 150.8 (CH), 146.6 (C), 129.0 (CH), 115.4 (C), 114.5 (C), 49.9 ($CH_2$), 43.7 ($CH_2$), 33.0 ($CH_2$), 30.5 ($CH_2$), 30.4 ($CH_2$), 30.3 ($CH_2$), 28.4 ($CH_2$), 23.7 ($CH_2$), 14.4 ($CH_3$). ESI-HRMS calcd for $C_{15}H_{26}N_5^+$, (M+H)$^+$, 276.2183. found 276.2181.

Results and Discussion

Commonly used antibiotics in *H. pylori* infections include amoxicillin, metronidazole and tetracycline. The anti-*H. pylori* effects of selected compounds were compared to those antibiotics in common use.

In most bacteria, MTANs are expressed and catalyze the hydrolysis of the N-ribosidic bonds of 5'-methylthioadenosine and S-adenosylhomocysteine. The two reactions are involved in bacterial quorum sensing, sulfur recycling via S-adenosylmethionine and polyamine synthesis[13]; however, most bacterial MTANs are not essential for bacterial proliferation as judged by planktonic growth conditions.

Bacterial genome analysis predicts the HpMTAN-mediated pathway for menaquinone biosynthesis to be rare, but also to be present in *Campylobacter* species[4]. *Campylobacter jejuni* is the world's leading cause of bacterial gastroenteritis[11].

Drug resistance has developed quickly in *H. pylori*, and currently, approximately 30% of *H. pylori* infection are resistant to single-agent first line drugs[12]. As a result, the current approach commonly uses triple-agent therapy for *H. pylori* infections and includes two antibiotics with different mechanisms of action. Even with triple-agent therapy, more than 20% of *H. pylori* infections are not readily eradicated[2]. Resistance in the *H. pylori* population is no doubt partially due to exposing *H. pylori* to broad spectrum antibiotics during the treatment of other bacterial infections. In addition, current eradication of *H. pylori* requires antibiotics for two weeks or longer and there is an increase in the development of resistance if treatment is interrupted. Table 1 summarizes the dissociation constants versus *H. pylori* MTAN and the MIC90 values against *H. pylori* for specific compounds of the invention. Drug combinations using these compounds may also address current issues of antibiotic resistance.

TABLE 1

Acyclic Amine Inhibitors of *Helicobacter pylori* MTAN and their MIC90 values against *H. pylori*.

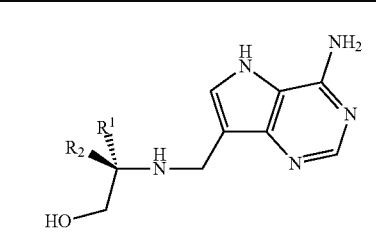

| Compound number, $R^1$ =, $R^2$ = | Inhibition of *H. pylori* MTAN | | Inhibition of *H. pylori* growth |
|---|---|---|---|
| | Ki (nM) | Ki* (nM) | MIC90 (ng/mL) |
| (V.2) $R^1$ = Pyrazin-2-ylthiomethyl, $R^2$ = H | 0.10 ± 0.01 | | 8 |

TABLE 1-continued

Acyclic Amine Inhibitors of *Helicobacter pylori* MTAN and their MIC90 values against *H. pylori*.

| Compound number, $R^1 =$, $R^2 =$ | Inhibition of *H. pylori* MTAN Ki (nM) | Ki* (nM) | Inhibition of *H. pylori* growth MIC90 (ng/mL) |
|---|---|---|---|
| (S.2) $R^1$ = n-Pentyl, $R^2$ = H | 0.10 ± 0.01 | | 8 |
| (T.2) $R^1$ = n-Hexyl, $R^2$ = H | 0.030 ± 0.003 | | 8 |
| (Q.2) $R^1$ = n-Butylthiomethyl, $R^2$ = H | 0.11 ± 0.01 | | 16 |
| (E.1) $R^1$ = n-Butyl, $R^2$ = H | 0.9 ± 0.2 | | 16 |
| (D.1) $R^1$ = n-Propyl, $R^2$ = H | 1.2 ± 0.4 | | 40 |

TABLE 1-continued

Acyclic Amine Inhibitors of *Helicobacter pylori* MTAN and their MIC90 values against *H. pylori*.

| Compound number, $R^1 =$, $R^2 =$ | Inhibition of *H. pylori* MTAN Ki (nM) | Ki* (nM) | Inhibition of *H. pylori* growth MIC90 (ng/mL) |
|---|---|---|---|
| (U.2) $R^1 = H$, $R^2 = $ n-Nonyl | 0.12 ± 0.01 | | 80 |
| (L.3) $R^1 = $ n-Benzylthiomethyl, $R^2 = H$ | 0.7 ± 0.1 | 0.21 ± 0.02 | >80 |
| (F.1) $R^1 = H$, $R^2 = $ n-Butyl | 0.8 ± 0.1 | | >80 |
| (K.3) $R^1 = $ 4-Chlorophenylthiomethyl, $R^2 = H$ | 0.9 ± 0.1 | | >80 |

TABLE 1-continued

Acyclic Amine Inhibitors of *Helicobacter pylori* MTAN and their MIC90 values against *H. pylori*.

| Compound number, R¹ =, R² = | Inhibition of *H. pylori* MTAN | | Inhibition of *H. pylori* growth |
|---|---|---|---|
| | Ki (nM) | Ki* (nM) | MIC90 (ng/mL) |
| (Y.1) R¹ = (S)-1-Hydroxy-2-methylthioeth-1-yl, R² = H (Synthesis in WO 08 030118) | 5 ± 2 | | >80 |
| (B.1) R¹ = Methyl, R² = H | 13 ± 2 | | >80 |
| (J.1) R¹ = Phenyl, R² = H | 13 ± 2 | | >80 |
| (C.1) R¹ = Ethyl, R² = H | >5 | | >80 |
| (Z.1) R¹ = H, R² = (R)-1-Hydroxy-2-methylthioeth-1-yl (Synthesis in WO 08 030118) | >10 | | >80 |

TABLE 1-continued

Acyclic Amine Inhibitors of *Helicobacter pylori* MTAN and their MIC90 values against *H. pylori*.

| Compound number, R¹ =, R² = | Inhibition of *H. pylori* MTAN | | Inhibition of *H. pylori* growth |
|---|---|---|---|
| | Ki (nM) | Ki* (nM) | MIC90 (ng/mL) |
| (P.4) R¹ = Imidazol-4-ylmethyl, R² = H | >50 | | >80 |
| (R.2) R¹ = n-Heptylthiomethyl, R² = H | 0.05 ± 0.01 | | 80 |
| (G.1) R¹ = Propyl, R² = H | >5 | | >80 |
| (H.1) R¹ = 2-Methylpropyl, R² = H | >5 | | >80 |
| (W.1) R¹ = Methylthiomethyl, R² = H | >5 | | >80 |

TABLE 1-continued

Acyclic Amine Inhibitors of *Helicobacter pylori* MTAN and their MIC90 values against *H. pylori*.

| Compound number, R¹ =, R² = | Inhibition of *H. pylori* MTAN | | Inhibition of *H. pylori* growth |
|---|---|---|---|
| | Ki (nM) | Ki* (nM) | MIC90 (ng/mL) |
| (X.1) R¹ = H, R² = Methylthiomethyl | >5 | | >80 |
| (I.1) R¹ = (S)-2-Butyl, R² = H | >5 | | >80 |

TABLE 2

Other Acyclic Amine Inhibitors of *Helicobacter pylori* MTAN and their MIC90 values against *H. pylori*.

| Compound number, R = | Inhibition of *H. pylori* MTAN | | Inhibition of *H. pylori* growth |
|---|---|---|---|
| | Ki (nM) | Ki* (nM) | MIC90 (ng/mL) |
| (AA.1) R = n-Octyl | 0.2 ± 0.04 | | >80 |

TABLE 2-continued

Other Acyclic Amine Inhibitors of *Helicobacter pylori* MTAN and their MIC90 values against *H. pylori*.

| Compound number, R = | Inhibition of *H. pylori* MTAN Ki (nM) | Ki* (nM) | Inhibition of *H. pylori* growth MIC90 (ng/mL) |
|---|---|---|---|
| 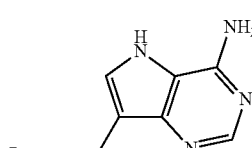 (A.1) R = 2-Hydroxyethyl | >5 | | >80 |

Example 2

In Vitro Activity of Compound T.2 (Hexyl-SerMe-Immucillin A)

These following experiments were conducted at UNT Health Science Center (Study lead: William J Weiss, Director of Pre-Clinical Services), Fort Worth, Tex., USA.

(a) Sample Plate Preparation: Aliquots of a 2-fold serial dilution of Hexyl-SerMe-Immucillin A (from 62.5 µg/mL-6.25 µg/mL in DMSO, 0.02 mL) were mixed into separate 2 mL molten MHIIb agar, and poured into separate wells on each well of a 12-well plate, allowed to set for 20-30 minutes and dry in a biosafety cabinet for 10 minutes prior to Inoculation.

(b) Inoculation: Frozen inoculate stock of *H. pylori* strains UNT020-1 (Sydney Strain SS1) and UNT189-1 (ATCC43504) was separately streaked onto Columbia+5% sheep blood agar and microaerophilically incubated for 72 h at 37° C. The plate cultures of the *H. pylori* strains were then harvested in 0.9% sterile saline solution and the OD at 530 nm of the suspension was determined. The OD of each suspension was adjusted to 1.5-2.0 by dilution into 0.9% sterile saline. The UNT020-1 suspension was further diluted 2:5, but the UNT189-1 suspension was not further diluted, and these were used to inoculate the agar plates. Samples of the suspensions (3 µL) were spotted onto the MHIIb agar wells in the 12-well plate. The CFU/mL of each inoculum was confirmed by generating a 10-fold serial dilution of each inoculum in 0.9% sterile saline and spotting 8 µL of each dilution onto Columbia+5% sheep blood agar plates. After allowing the spots to dry for 10 min, the plates were placed into a microaerophilic chamber and incubated at 37° C. for 72 h.

Results: The Minimum Inhibitory Concentrations (MICs) for the Hexyl-SerMe-immucillin A was determined against *H. pylori* isolates UNT020-1 (Sydney Strain SS1) and UNT189-1 (ATCC43504). Hexyl-SerMe-Immucillin A exhibited excellent activity against the two *H. pylori* strains with an MIC of 1.9 ng/mL in each case.

The Concentration of Compound T.2 (Hexyl-SerMe-Immucillin A) in the Gastric Mucin of Mouse Following a Single Oral Dose at 10 mg/kg These following experiments were conducted at UNT Health Science Center (Study lead: William J Weiss, Director of Pre-Clinical Services), Fort Worth, Tex., USA.

(a) Oral Dosing of Mice with 10 mg/kg Hexyl-SerMe-Immucillin A: Female C57/BL6 mice ranging from 5-6 weeks in age and 18-22 grams in weight (Harlan Laboratories) were dosed by oral gavage with of Hexyl-SerMe-Immucillin A (0.4 mL of a 0.5 mg/mL solution in water for injection).

(b) Mucin Sampling: Mice (3 mice/time point) were euthanized via $CO_2$ inhalation at 0.25, 0.5, 1, 2, 4, 8, 12 and 24 h, then the mucin layer was scraped from the longitudinally dissected stomach using a glass slide, collected and weighed.

(c) Preparation of Gastric Mucin Homogenates: Approximately 30 mg of mouse mucin was weighted into a 2 mL homogenizer tube (prefilled with 3.0 mm i.d. zirconium beads) and mixed with 0.2 mL PBS buffer. This was homogenized for 3 min at 4,000 rpm in a Beadbug D1030 (Benchmark Scientific) homogenizer.

(d) Extraction of Gastric Mucin Homogenates: Samples of mucin homogenate (50 µL) and of internal standard (see below) in water (10 µL) were treated with trichloroacetic acid (30% w/v, 30 µL), diluted with water (160 µL), vortexed for 10 sec and sonicated for 10 min, then centrifuged at 14,500 rpm for 5 min. A sample of the supernatant (160 µL) was transferred into autosampler vials. The internal standard was Butylthio-DADMe-Immucillin-H at 5.0 and 20.0 µg/mL.

(f) HPLC-MS-MS Analysis: Aliquots of supernatant (10 µL) were injected for analysis on Surveyor HPLC system (Thermo) fitted with an ACE 3 C18 Column (50×3 mm, 3 µm particles), with gradient elution at 30° C. with 400 µL/min mobile phase comprised of mixtures of 0.1% trifluoroacetic acid in water (A) and methanol (B) as follows: 0-5 min, A:B 9:1; 5-6.1 min, A:B 1:9; 6.1-10 min A:B 9:1. Hexyl-SerMe-Immucillin A eluted at 4.41±0.003 min. Detection was ESI MS/MS using a LCQ Deca (Thermo) in selected-reaction monitoring (SRM) positive mode using the MS/MS event m/z 292.2→147.2 and ion spray voltage of 4.5 kV.

(g) Results: The results for Hexyl-SerMe-Immucillin A in gastric mucin following administration of 10 mg/kg by oral gavage in mice are shown in the Table and FIGURE below. A high and prolonged level of Hexyl-SerMe-Immucillin A was detected in the gastric mucin, with the $C_{max}$ value was 65.5 µg/g, total exposure [$AUC_{(0-inf)}$] was 78.6 µg-h/g and the terminal half-life was 2.72 h.

TABLE 3

The concentration of Hexyl-SerMe-Immucillin A in mouse gastric mucin versus time following a single dose of 10 mg/kg PO.

| Time | Hexyl-SerMe-Immucillin A (µg/g) | | | | | |
|---|---|---|---|---|---|---|
| (h) | Animal-1 | Animal-2 | Animal-3 | Mean | SD | SEM |
| 0.25 | 60.42 | 64.36 | 45.91 | 56.89 | 9.71 | 4.34 |
| 0.50 | 46.24 | 90.18 | 60.18 | 65.53 | 22.46 | 10.04 |
| 1.00 | 20.39 | 12.20 | 12.04 | 14.88 | 4.77 | 2.13 |
| 2.00 | 2.02 | 1.08 | 16.24 | 6.44 | 8.49 | 3.80 |
| 4.00 | 0.67* | 3.74 | 0.91 | 1.77 | 1.71 | 0.76 |
| 8.00 | 0.65* | 1.62 | 0.53* | 0.93 | 0.60 | 0.27 |
| 12.0 | 0.96 | 0.95 | 0.33* | 0.74 | 0.36 | 0.16 |
| 24.0 | 0.54* | 0.39* | 0.30* | 0.41 | 0.12 | 0.06 |

*below LLOQ

REFERENCES

1. Kuipers, E. J., Thijs, J. C. & Festen, H. P. *Aliment. Pharm. Therap.* 9 Suppl 2, 59-69 (1995).
2. Malfertheiner, P. et al. *Lancet* 377, 905-913 (2011).
3. Popp, J. L., Berliner, C. & Bentley, R. *Anal. Biochem.* 178, 306-310 (1989).
4. Li, X., Apel, D., Gaynor, E. C. & Tanner, M. E. *J. Biol. Chem.* 286, 19392-19398 (2011).
5. Dairi, T. *J. Antibiot.* 62, 347-352 (2009).
6. Gutierrez, J. A. et al. *Nature Chem. Biol.* 5, 251-257 (2009).
7. Longshaw, A. I., Adanitsch, F., Gutierrez, J. A., Evans, G. B., Tyler, P. C., Schramm, V. L. Design and Synthesis of Potent "Sulfur-Free" Transition State Analogue Inhibitors of 5'-Methylthioadenosine Nucleosidase and 5'-Methylthioadenosine Phosphorylase. *J. Med. Chem.* 53, 6730-6746 (2010).
8. Singh, V. et al. Femtomolar transition state analogue inhibitors of 5'-methylthioadenosine/S-adenosylhomocysteine nucleosidase from *Escherichia coli*. *J. Biol. Chem.* 280, 18265-18273 (2005).
9. Singh, V. & Schramm, V. L. *J. Am. Chem. Soc.* 129, 2783-2795 (2007).
10. Gutierrez, J. A. et al. Picomolar inhibitors as transition-state probes of 5'-methylthioadenosine nucleosidases. *ACS Chem. Biol.* 2, 725-734 (2007).
11. Man, S. M. *Nat. Rev. Gastroenterol. Hepatol.* 8, 669-685 (2011)
12. Vakil, N. *Am. J. Gastro.* 104, 26-30 (2009).
13. Dondoni, A.; Perrone, D.; *Org. Synth., Coll.* Vol. 10. 320 (2004); *Org. Synth.* 77, 64, (2000).
14. Madrigal, B.; Puebla, P.; Caballero, E.; Pelaez, R.; Gravalos, D. G.; Medarde, M. *Arch. Pharm. Pharm. Med. Chem.* 334, 177-179 (2001).
15. Goswami, K.; Paul, S.; Budge, S. T.; Sinha, S. *Tetrahedron* 68, 280-286 (2012).
16. Paleček, J.; Kvičala, J.; Paleta, O. *J. Fluorine Chem.* 113, 177-18 (2002).
17. Ksander, G. M.; de Jesus, R.; Yuan, A.; Ghai, R. D.; Trapani, A; McMartin, C.; Bohacek, R. *J. Med. Chem.* 40. 495-505 (1997).
18. Clinch, K.; Evans, G. B.; Fröhlich, R. F. G.; Gulab, S. A.; Gutierrez, J. A.; Mason, J. M.; Schramm, V. L.; Tyler, P. C.; Woolhouse, A. D. *Bioorg. Med. Chem. Lett.* 20, 5181-5187 (2012).
19. PCT International Patent Application Publication No. WO 2008/030118, published Mar. 13, 2008.

What is claimed is:

1. A method of treating a *Helicobacter pylori* (*H. pylori*) infection in a subject comprising administering to the subject a compound in an amount effective to inhibit growth of *H. pylori*, wherein the compound has the formula

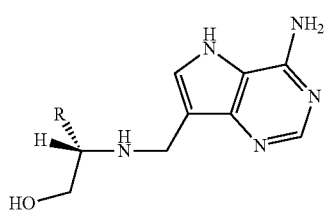

wherein R is Q or $CH_2SQ_1$, wherein Q is C1-C9 alkyl, aryl, heteroaryl, aralkyl, or C4-C7 cycloalkyl, where Q is optionally substituted with one or more halogen, OH and/or $NH_2$ groups, and wherein $Q_1$ is C4-C9 alkyl, aryl, heteroaryl, aralkyl, or C4-C7 cycloalkyl, where $Q_1$ is optionally substituted with one or more halogen, OH and/or $NH_2$ groups, or a pharmaceutically acceptable salt thereof, or an ester thereof.

2. The method of claim 1, wherein R is Q.
3. The method of claim 1, wherein R is $CH_2SQ_1$.
4. The method of claim 1, wherein Q is C1-C9 alkyl.
5. The method of claim 1, wherein Q or $Q_1$ is C4-C7 cycloalkyl.
6. The method of claim 1, wherein Q or $Q_1$ is aryl.
7. The method of claim 1, wherein Q or $Q_1$ is heteroaryl.
8. The method of claim 1, wherein Q or $Q_1$ is aralkyl.
9. The method of claim 1, wherein Q or $Q_1$ is aryl, heteroaryl or aralkyl substituted with a halogen.
10. The method of claim 1, wherein R is Q, wherein Q is C2-C9 linear alkyl, aryl, heteroaryl, aralkyl, or C4-C7 cycloalkyl, and wherein Q is optionally substituted with one or more halogen, OH and/or $NH_2$ groups.
11. The method of claim 9, wherein the halogen is at an ortho, meta or para position.
12. The method of claim 1, wherein the halogen is Cl, F, Br or I.
13. The method of claim 1, wherein Q is C3-C9 linear alkyl or heteroaryl.
14. The method of claim 1, wherein the compound is selected from the group consisting of

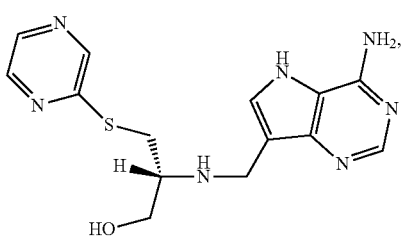

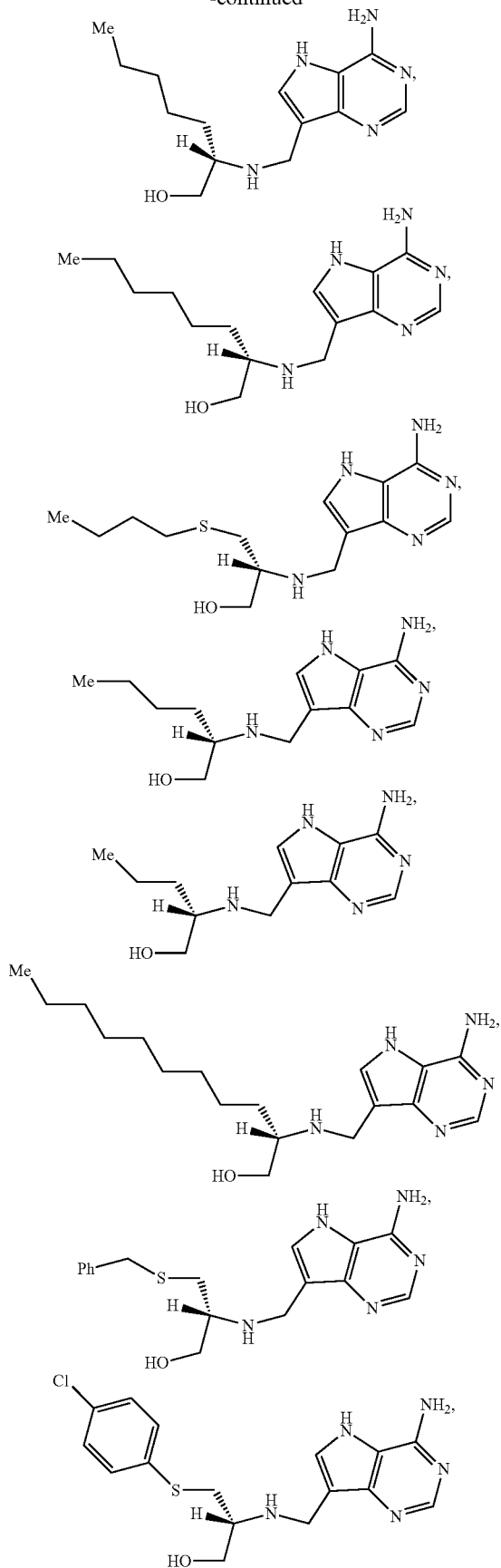
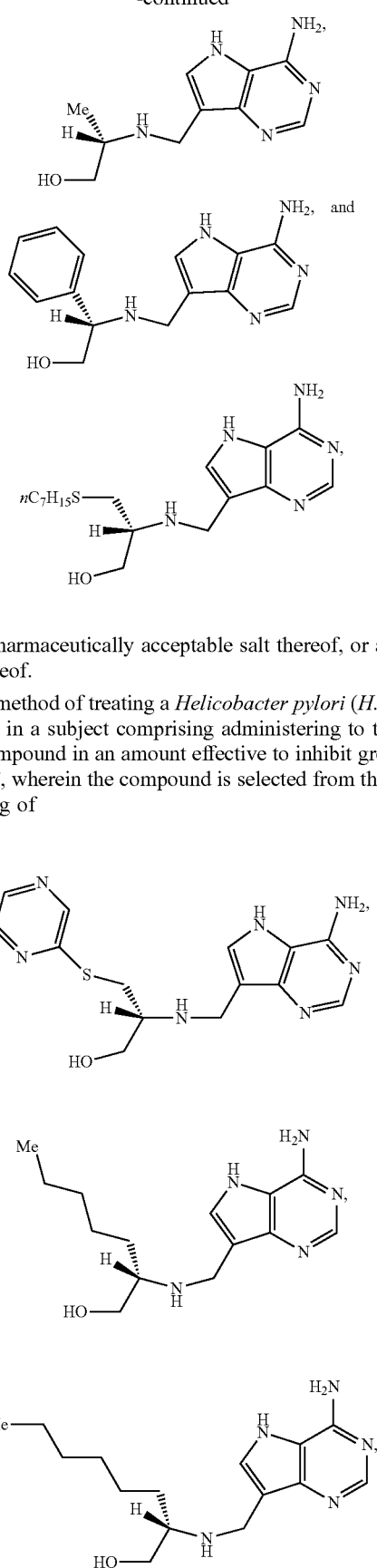
or a pharmaceutically acceptable salt thereof, or an ester thereof.
15. A method of treating a *Helicobacter pylori* (*H. pylori*) infection in a subject comprising administering to the subject a compound in an amount effective to inhibit growth of *H. pylori*, wherein the compound is selected from the group consisting of -continued

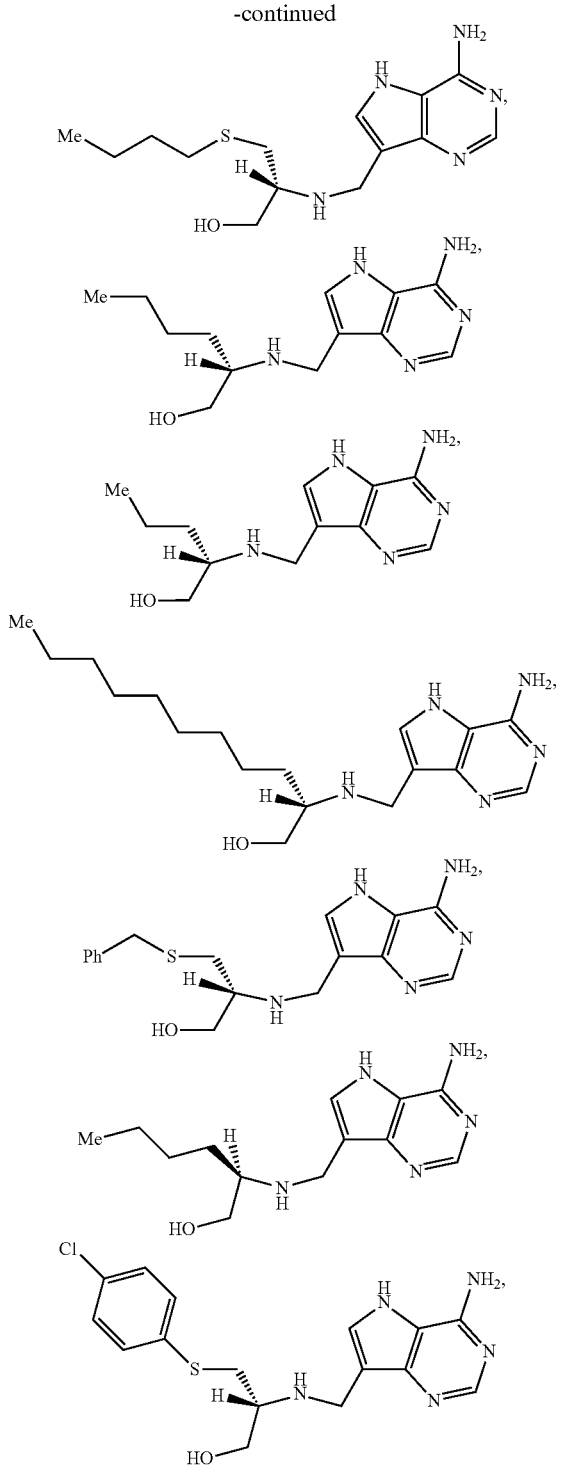

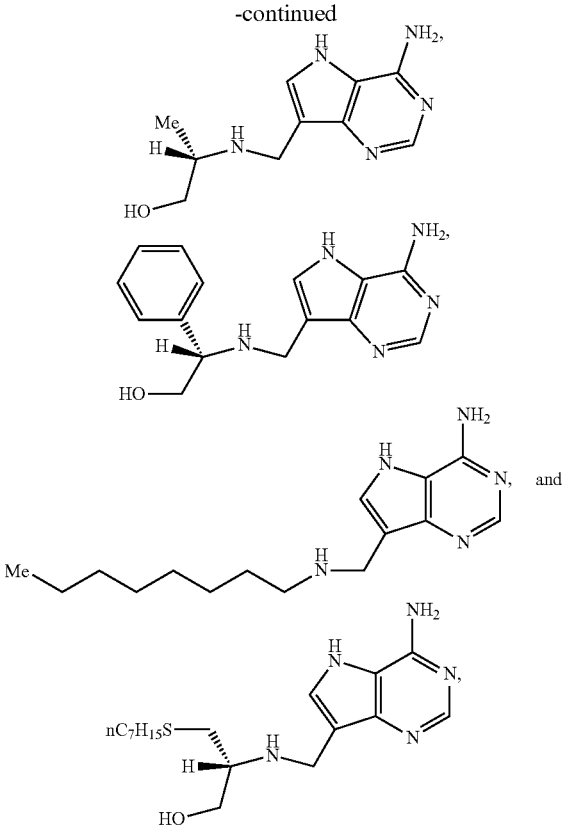

or a pharmaceutically acceptable salt thereof, or an ester thereof.

16. The method of claim 1, wherein the compound is administered in an amount that is effective to inhibit *H. pylori* 5′-methylthioadenosine nucleosidase (MTAN).

17. The method of claim 1, wherein the compound inhibits growth of *H. pylori* but does not inhibit the growth of one or more bacterium selected from the group consisting of *E. coli, V. cholerae, S. aureus, K. pneumoniae, S. flexneri, S. enterica* and *P. aeruginosa*.

18. The method of claim 17, wherein the compound does not inhibit the growth of all of *E. coli, V. cholerae, S. aureus, K. pneumoniae, S. flexneri, S. enterica* and *P. aeruginosa*.

19. The method of claim 1, wherein the compound is more effective in inhibiting growth of *H. pylori* than amoxicillin, metronidazole or tetracyclin.

20. The method of claim 1, wherein the subject has a peptic ulcer.

21. The method of claim 1, wherein the subject has a gastric ulcer or a duodenal ulcer.

22. The method of claim 1, wherein the compound is administered orally.

* * * * *